United States Patent
Fulton, III

(10) Patent No.: US 9,545,195 B2
(45) Date of Patent: Jan. 17, 2017

(54) PATIENT CONTROLLED DENTAL DEVICE AND METHOD

(71) Applicant: NDENTAL, LLC, Telluride, CO (US)

(72) Inventor: Richard Eustis Fulton, III, Grand Junction, CO (US)

(73) Assignee: AWESTRUCK DENTAL LLC, Telluride, CO (US)

( * ) Notice: Subject to any disclaimer, the term of this patent is extended or adjusted under 35 U.S.C. 154(b) by 0 days.

(21) Appl. No.: 14/504,518

(22) Filed: Oct. 2, 2014

(65) Prior Publication Data

US 2015/0093716 A1    Apr. 2, 2015

Related U.S. Application Data

(60) Provisional application No. 61/961,106, filed on Oct. 2, 2013, provisional application No. 61/967,319, filed on Mar. 13, 2014, provisional application No. 61/997,780, filed on Jun. 9, 2014.

(51) Int. Cl.
    *A61B 1/24*    (2006.01)
    *A61C 17/06*   (2006.01)
    *A61B 1/32*    (2006.01)

(52) U.S. Cl.
    CPC . *A61B 1/24* (2013.01); *A61B 1/32* (2013.01); *A61C 17/04* (2013.01); *A61C 17/043* (2013.01)

(58) Field of Classification Search
    CPC .......... A61C 17/04; A61C 17/043; A61B 1/24
    USPC ............................................. 433/93; 604/902
    See application file for complete search history.

(56) References Cited

U.S. PATENT DOCUMENTS

| | | | | |
|---|---|---|---|---|
| 160,604 | A | * | 3/1875 | Lewis ................... A61C 5/122 433/137 |
| 637,970 | A | * | 11/1899 | Nyman ............... A61C 17/043 433/93 |
| 1,042,133 | A | * | 10/1912 | Marshall ................. A61B 1/24 433/93 |
| 1,053,965 | A | * | 2/1913 | Barghausen et al. A61C 17/043 433/93 |
| 1,557,744 | A | * | 10/1925 | Tobriner .............. A61C 17/043 433/91 |
| 1,731,322 | A | | 10/1929 | Riddle |
| 1,930,712 | A | | 10/1933 | Girvin |
| 3,090,122 | A | | 5/1963 | Erickson |
| 3,091,859 | A | * | 6/1963 | Baughan .............. A61C 17/043 433/94 |

(Continued)

OTHER PUBLICATIONS

International search report and written opinion dated Jan. 7, 2015 for PCT Application No. US2014/058904.

(Continued)

*Primary Examiner* — Ralph Lewis
(74) *Attorney, Agent, or Firm* — Wilson, Sonsini, Goodrich & Rosati

(57) ABSTRACT

A device for helping maintain a mouth of a patient in an open position during a dental procedure may include a tooth engaging portion including at least one groove for accepting at least one lower tooth of the patient's lower jaw, an extension portion that extends away from the tooth engaging portion, and a handle that extends down from the extension portion and ends in a caudal end. The caudal end of the handle and the groove of the tooth engaging portion lie along a longitudinal axis drawn through a center of the groove.

40 Claims, 16 Drawing Sheets

(56) References Cited

U.S. PATENT DOCUMENTS

| | | | | |
|---|---|---|---|---|
| 3,101,543 | A | * | 8/1963 | Baughan .............. A61C 17/043 |
| | | | | 433/94 |
| 3,802,081 | A | * | 4/1974 | Rogers ................. A61C 17/043 |
| | | | | 433/93 |
| 4,112,934 | A | * | 9/1978 | Rizk ........................ A61C 5/14 |
| | | | | 433/142 |
| 4,158,916 | A | | 6/1979 | Adler |
| 4,259,067 | A | | 3/1981 | Nelson |
| 4,259,068 | A | | 3/1981 | Stephens |
| 5,462,435 | A | | 10/1995 | Young |
| 5,588,836 | A | | 12/1996 | Landis et al. |
| 5,931,670 | A | | 8/1999 | Davis |
| 6,030,217 | A | | 2/2000 | Fletcher |
| 6,213,772 | B1 | | 4/2001 | Costello |
| 2006/0008764 | A1 | | 1/2006 | Abo |
| 2007/0082319 | A1 | | 4/2007 | Fletcher et al. |
| 2010/0305510 | A1 | | 12/2010 | Spinoza |
| 2016/0270878 | A1 | | 9/2016 | Fulton, III |

OTHER PUBLICATIONS

European Search Report and Opinion dated Aug. 16, 2016 for EP No. 14851077.9.
International Search Report dated Sep. 2, 2016 for International Application No. PCT/US2016/024773.

* cited by examiner

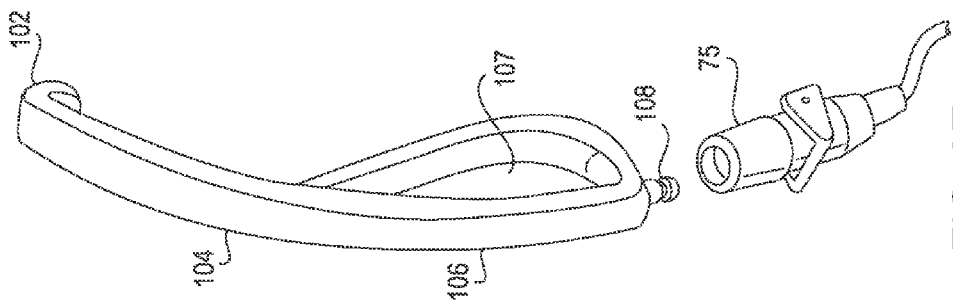
FIG. 9E
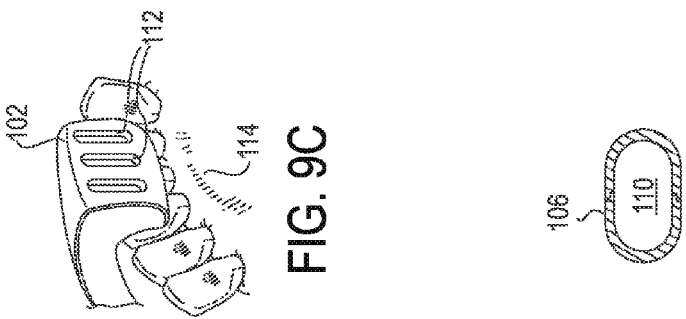
FIG. 9C
FIG. 9D
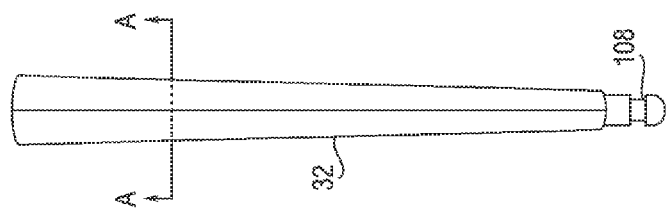
FIG. 9B
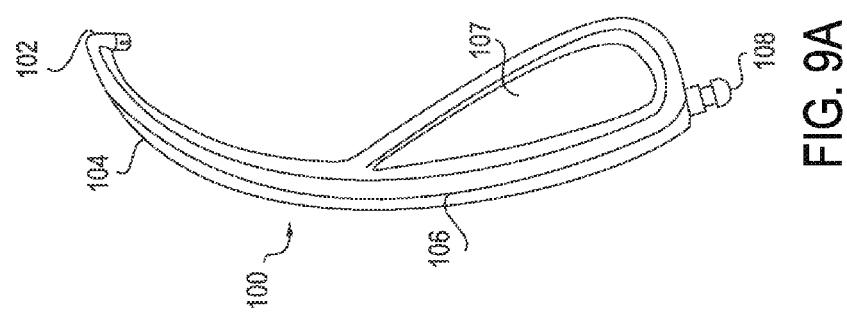
FIG. 9A

PATIENT CONTROLLED DENTAL DEVICE AND METHOD

CROSS-REFERENCE TO RELATED APPLICATIONS

The present application claims priority to U.S. Provisional Patent Application Ser. Nos. 61/961,106, entitled "Patient Controlled Dental Device," filed on Oct. 2, 2013; 61/967,319, entitled "Patient Controlled Dental Device," filed on Mar. 13, 2014; and 61/997,780, entitled "Patent Controlled Dental Device and Method," filed on Jun. 9, 2014. All of the patent applications listed above are hereby incorporated by reference herein, in their entirety.

BACKGROUND

Dental procedures are very common and are necessary for proper dental health, whether it be dental fillings, dental crown applications, root canals, orthodontic work, periodontal surgery, dental cleaning, and many other procedures. One common problem with these dental procedures is that the patient must maintain an open mouth for extended periods of time. The dentist, dental assistant, or dental hygienist must have adequate exposure to access the site to be treated. While opening of the mouth for short periods of time is not problematic for most patients, many, if not most, patients do have difficulty maintaining an open mouth for the extended periods of time required for many dental procedures. All dental patients have at least some difficulty opening their mouths for prolonged periods, as this prolonged opening fatigues the muscles and becomes uncomfortable. Most patients just accept that going to the dentist is uncomfortable and just tolerate the discomfort. Fifty percent of patients have significant difficulty keeping the mouth open for any procedure. This percentage increases with the length of time of the procedure. Elderly, young, and patients on psychotropic drugs have more difficulty that others, but virtually all patients have discomfort opening the mouth for any period of time.

This rather high figure may reflect the prevalence of temporomandibular joint disorders (TMD) in the general population. Epidemiological studies have revealed an average of 30%-44% prevalence of TMD in the general population. All of these patients will experience difficulty at the dentist, with either limited mouth opening or with pain and discomfort in the jaw muscles from straining to keep the mouth open or both. There is also a subset of the population that does not have TMD but that does have difficulty and/or pain with limited mouth opening, due to other causes of muscle tightness. Examples of such causes of difficulty with mouth opening include bruxism, clenching, stress, psychological issues, and others. This segment accounts for as much as 20% of the population. Hence, well over 50% of the population may have difficulty with prolonged mouth opening for dental procedures.

The typical reason for difficulty with prolonged mouth opening is muscle fatigue and spasm that initially becomes uncomfortable but progresses to become quite painful. The human mouth is a simple hinge, with the mandible articulated with the skull at the temporomandibular joint. The muscle systems that cause the mandible to close are mainly the large masseter muscles and the temporalis muscles. These are robust and responsible for forceful chewing, mastication, clenching, bruxing, etc. The corresponding muscles responsible for opening the mouth are mainly the small and delicate pterygoid muscles. This causes a disparity in the opposing muscle groups, which is not of importance in the normal function of the mouth during usual activities such as eating, drinking, speaking, and the like. However, prolonged opening of the mouth is affected by, and very difficult because of, the size, disparity, and arrangement of the opposing muscle sets. The smaller pterygoid muscles tire after several minutes of prolonged opening, causing discomfort and actual pain.

This creates a dilemma, as the dental practitioner must have access to the oral cavity to perform the necessary task, but frequently the simple act of holding the mouth open is uncomfortable to the patient. Devices that assist in holding the mouth open have been in use for many years for this reason. These consist of bite blocks, which are simple wedge devices placed between the teeth to prop open the mouth by creating a consistent space between the upper teeth and lower teeth by depressing the mandible. Bite blocks are used on one side of the jaw or the other to allow access for procedures, and this asymmetrical use can strain the temporomandibular joints, often triggering joint pain. Use of a bite block also creates a persistent and continuous stretching of all the muscles that affect the depression of the mandible, i.e., the pterygoids, or elevation of the mandible, i.e., the masseters and the temporalis groups. These devices offer no period of relaxation for the muscles to recover from the stress of the continuous stretching. This lack of a relaxation period can result in pain and discomfort to the patient. The bite blocks also occupy space within the oral cavity and impede access or exposure to the specific area that needs attention or treatment.

Other known devices have been developed that prop the mouth open but are almost universally awkward to employ, as they also frequently inhibit access to all parts of the oral cavity and the dental practitioner must navigate around these devices to perform the necessary and intended maneuvers. They also provide a continuous and persistent stretching of the musculature, which results in discomfort while attempting to assist in keeping the mouth open. The bite blocks commonly used actually stimulate contraction of the muscles responsible for closing the mouth and accentuate the problems and difficulties.

In U.S. Pat. No. 6,030,217, Fletcher describes a device comprised of a flexible mouth piece that fits over the lower front teeth and an elongated flexible member attached at one end to the mouth piece and the other end to a handhold object. Fletcher's device may suffer from limitations that preclude optimal functioning to assist with opening the mouth and maintaining it open in a comfortable position in a safe manner. For instance, the mouth piece has sufficient flexibility to permit the mouth piece to bend and release from the lower teeth when the flexible member is subjected to a selected threshold tension. This, in essence, means that the mouth piece will typically flex and become disengaged from the lower teeth if the patient exerts more downward force than the mouth piece will tolerate. With significant downward force being exerted and an abrupt release by the mouth piece, the mouth piece may be forcefully be propelled or pulled downward toward the hand. As soon as the trailing edge clears the teeth, it may engage the lower lip with significant abrupt downward force, and at the very least, bruise the lower lip if not lacerate it. As well, the mouthpiece may be propelled as a missile toward the hand, where it may impact the hand, fingers, or other body part or even the dentist or dental assistant. Just the thought of a piece of plastic flying about the dental operatory, contaminating equipment and personnel with saliva, enough to discourage the use of such a device.

Additionally, since any incremental tension may be at least partially, if not mostly, absorbed by the flexible mouth piece of Fletcher, rather than transferred to the mandible, the mouth piece will bend or deform, instead of providing additional consistent, graded and gradual downward pressure on the mandible. Slow and gradual increases in tension downward are often needed for maximum relaxation and stretching. Hence, the flexible mouthpiece of Fletcher may be limited for this reason as well.

Moreover, the elongated flexible member of Fletcher can create an unlimited number of angles and directions in which the downward force may be directed. The elongated flexible member of Fletcher may introduce variability in the use of the device, which also can be a safety issue. The teeth may be accustomed to downward pressure and are very stable when pressure is in the same plane as the long axis of the tooth. If the force is downward and forward, or downward and to one side or the other, the tooth or teeth may be loosened or tilted. Marginally loose teeth from periodontal disease or other causes could be loosened even more than at their resting state. The temporomandibular joint (TMJ) may also be damaged by inappropriately directed forces. Tension forward or outward may even dislocate the TMJ, and tension to the side may cause TMJ dysfunction or worsen TMJ preexisting conditions. With so many variations in the direction of the force, it may be exceedingly difficult to align the flexible member, the mouth piece and the handhold object so that the proper direction of the force is maintained during the entire dental procedure, which may last for an hour or longer. Hence, the flexible member of Fletcher may be convenient to connect the mouth piece with the handhold object, but it may be dangerous to the patient and the staff for a number of reasons, and it may create unintended problems and difficulties.

Additionally, there may be a need for devices or methods that increase the degree of opening of the mouth beyond passive opening using the muscles of the jaw or opening with a simple assist device. Not only do patients experience discomfort from having the jaw open for protracted periods, but the limited exposure to the dental operative field constantly constrains the dental practitioner. The ability to open the mouth maximally diminishes with the time the mouth is open, as the muscles fatigue and less than a fully open position is sought for comfort reasons. The practitioner is forced to operate and perform procedures within the mouth, which is basically a small hole, and that hole becomes smaller with time. The wider the patient is able open the teeth, the better the exposure for the dental practitioner and the less tedious the work becomes.

No known prior art devices are targeted improving the degree of opening the mouth or providing more exposure as the procedure progresses. Bite blocks act as props, and the Fletcher device may either prop or distract the mouth open, but this is where these devices stop. The bite blocks are forced between the upper and lower molars and may actually trigger a reflex to bite down. They certainly do not continue to improve the degree of opening. The Fletcher device may assist in opening the mouth and may reduce the discomfort despite the significant limitations and safety issues it presents, but it does not continue to improve the opening of the mouth and continue to improve the exposure available to the dentist. While the prior art includes devices that attempt to address the mouth-opening problem, all of these devices have shortcomings, as discussed above.

Another major limitation of known prior art devices is that they are all placed into the mouth, in addition to other devices used in a procedure. In other words, they are additive devices and occupy valuable space in the mouth, which limits the access by the dentist or hygienist in addition to the other tools that may be used. For example, while many different tools and devices may be used during a dental procedure, suction is used almost universally in dental procedures. Hence, the known prior art devices must be inserted in addition to the suction apparatus. This may become awkward and confusing, for example, if the patient is responsible for the suction with one hand and the Fletcher prior art device with the other hand. More importantly, the space occupied by a combination of suction tube and the prior art devices may well impede access to the mouth by the dentist. There is the probability of simply having too many items in the mouth at one time to allow easy access.

Therefore, it would be very desirable to have improved devices and methods for maintaining a mouth in an open position for prolonged periods of time for dental procedures. Ideally, these devices and methods would provide improvements over the prior art devices and methods and would reduce or eliminate at least some of the discomfort and pain of maintaining an open jaw. Also ideally, such devices and methods should work well for patients while not overly obstructing the dentist's access to the mouth for performing procedures. The embodiments described herein will meet at least some of these objectives.

SUMMARY

To solve the dilemmas described above, of the need to maintain an open mouth for an extended period of time, to open the mouth beyond that which is achievable from natural active opening, and to do both comfortably, the devices and methods described herein may rely on several basic physiologic principles. By exploiting these principles, the dental procedure can be more comfortable for the patient and can be performed by the practitioner more quickly and without significant interruptions. The degree that the mouth can open comfortably will also be enhanced, providing better access to the mouth for the dental practitioner.

One of the physiologic principles of which the present devices and methods may take advantage is that the distraction of the mandible may be intermittent, rather than the consistent and persistent distraction necessary with the prior art devices. This intermittent distraction may allow the musculature to rest occasionally and temporarily recover from the stress of the stretching. A brief change in the degree of stretching is often all that is frequently needed to prevent the discomfort.

Another physiologic principle is that downward pressure on the mandible actually relaxes the large masseter, temporalis, and internal pterygoid muscles that close the mouth via a reflex. This is the same reflex that relaxes these muscles when chewing exerts downward pressure on the mandible and stops the chewing motion when the teeth touch.

Hence, distraction of the mandible downward will not only aid the opening muscles of mastication (suprahyoid and lateral pterygoid muscles), but can obviate much of the contraction of the much larger and more powerful closing muscles of mastication by stretching and relaxing them.

Another principle is that continued low level, graded, and incremental traction on a muscle will relax and stretch the muscle, thus elongating the muscle and inhibiting reflex contraction of the muscle. Continued low level traction or stretching will continue to elongate the muscle. Hence, a technique and device that employs at least some of these physiologic principles may cause the mouth to open wider than possible with just active opening (without an assist) by the patient.

Another principle is that the maximum distraction of the mandible will occur when the patient temporarily relaxes the distractive force when the dental practitioner is not directly engaged in intra oral manipulations or functions. This may happen intermittently, when the practitioner must change implements or instruments, drill bits, scalers, curettes, probes, etc. During this brief interlude, the patient can temporarily relax the distraction to provide relief to the stretched muscles. Subsequent stretching will be even more effective as a result of this intermittent relaxation, which cannot occur with the use of a bite block. It may also be problematic to allow relaxation using the Fletcher device, because the mouth piece may become dislodged if all of the tension on the flexible member is relaxed, as there would be no force to hold the mouth piece adjacent to the teeth. The inability to accommodate these important maneuvers often prevent the prior art devices from functioning optimally.

Moreover, embodiments of the present disclosure may allow the dental practitioner to encourage or prompt the patient to provide more distraction at certain times. Hence, while the patient may control the force and degree of depression of the mandible, the dental practitioner has input, so adequate exposure is provided. This feedback loop may be essential in providing adequate exposure to the practitioner while providing patient comfort. The feedback loop may be another physiological principle not shown to be exploited in the prior art devices.

The feedback loop may also go from patient to practitioner. The patient frequently is unable to articulate any meaningful message to the practitioner if prior art devices are used, essentially using grunts and garbled words. The devices of the present disclosure would allow verbal and other communication, as will be described further below.

Aspects of the present disclosure provide a device for helping maintain a mouth of a patient in an open position during a dental procedure. The device may include a tooth engaging portion comprising at least one groove for accepting at least one lower tooth of the patient's lower jaw, an extension portion that extends away from the tooth engaging portion, and handle that extends down from the extension portion and ends in a caudal end. The caudal end of the handle and the groove of the tooth engaging portion may lie along a longitudinal axis drawn through a center of the groove. The handle and the extension portion may comprise a solid, one-piece construct. At least part of the tooth engaging portion may comprise the solid, one-piece construct. The tooth engaging portion may comprise a distal end of the solid, one-piece construct, and a piece of material attached to the distal end of the one-piece construct, wherein the piece of material is softer than the one-piece construct.

The extension portion may be curved. The extension portion and the tooth engaging portion may be forked, and a space between two prongs of the tooth engaging portion and the extension portion may be configured to accept a suction tube. The caudal end of the handle may comprise a finger loop through which a finger of the patient may be extended to facilitate application of downward force. A traction member may further be included to be removably coupled with the handle, for applying downward force to the handle. For example, the traction member may be a weight. The device may also additionally include a suction member coupled with the tooth engaging portion and/or the extension portion. Another feature may be a tissue displacement member coupled with the tooth engaging portion and/or the extension portion, for displacing the cheek and/or tongue of the patient. Yet another feature may be a tensiometer coupled with the device to measure downward force applied to the device.

Aspects of the present disclosure may also provide a method of maintaining a mouth of a patient in an open position during a dental procedure. These methods may involve placing a groove of a tooth engaging portion of a mouth distraction device over at least one lower tooth in a lower jaw of the patient's mouth, and pulling down on a handle of the mouth distraction device in a direction along a longitudinal axis of the lower tooth to maintain the lower jaw in an open position relative to an upper jaw of the patient's mouth. The groove of the tooth engaging portion of the mouth distraction device and the handle of the tooth distraction device may lie along a common, distraction device longitudinal axis, and the distraction device longitudinal axis may lie along the longitudinal axis of the at least one tooth during the pulling step.

The pulling step and/or the placing step may be performed by the patient. After the pulling step, the pulling force from the handle may be released to allow the lower jaw to relax and the mouth to at least partially close, and the pulling step may be repeated to reopen the mouth. The groove may be placed over multiple lower front teeth.

The methods may also involve applying suction in the patient's mouth, using a suction device incorporated into or attached to the mouth distraction device. Also, a weight may be attached to the handle of the mouth distraction device to apply downward force. The cheek and/or tongue of the patient may also be displaced using a tissue displacement member incorporated into or attached to the mouth displacement device. A lip retractor means may be attached to or incorporated into the mouth distraction device to displace the lips laterally, vertically, or other directions to provide more exposure to the oral cavity. A tensiometer coupled with the device may be used to measure downward force applied to the device. After the pulling step, a suction device may be passed through an opening in the mouth distraction device and into the patient's mouth, and suction may be applied in the mouth with the suction device, while the distraction device maintains the mouth in an open position.

The mouth opening devices described herein may be constructed for children in more or less the same configurations as described herein, but smaller to accommodate the smaller mouth and teeth of children. Moreover, attachments may be provided to the device to create a more visually appealing device to children.

These and other embodiments and aspects are described in greater detail below, in relation to the attached drawing figures.

BRIEF DESCRIPTION OF DRAWINGS

FIGS. 9A-9E are side, front, close-up/perspective, end-on/cross-sectional, and posterior perspective views, respectively, of a mouth opening device with a built-in suction channel for connecting directly with a suction hose, according to many embodiments.

DETAILED DESCRIPTION

Figure 1A:
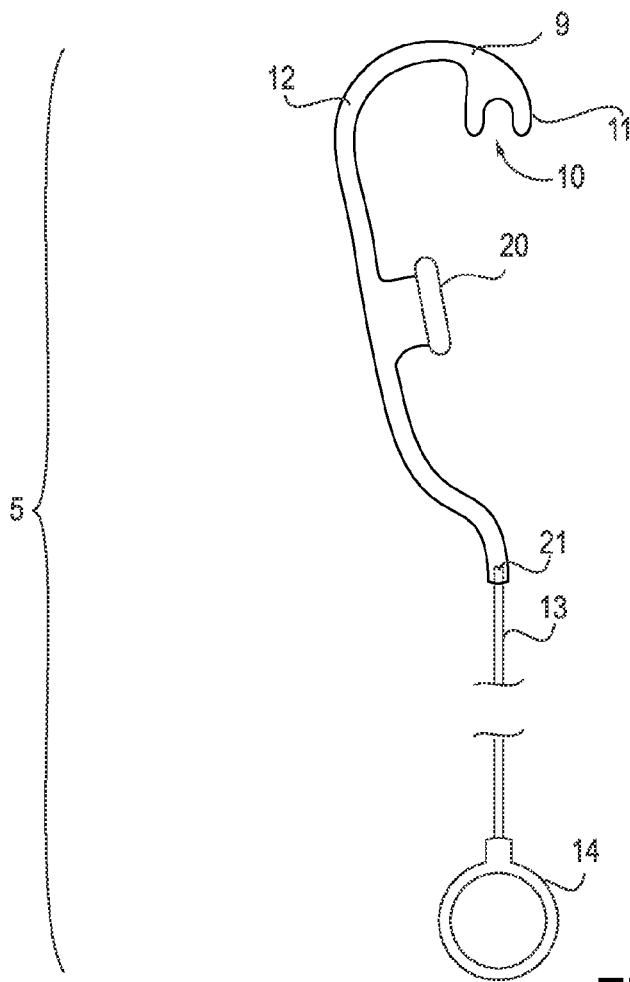
FIGS. 1A and 1B are side and top views, respectively, of a mouth opening device, according to many embodiments.

FIGS. 1A-1D illustrate a mouth opening device 5, from various perspectives (side view, top view, side view in a cross-sectional view of a mouth, and perspective view in a mouth, respectively). As illustrated in FIG. 1A, the device 5 may include a tooth piece (or "tooth component") 9, which may fit over at least one lower tooth, an extension component 12, which may extend out of the mouth and over the lower lip, extending caudally to a point under the chin and in more or less the same coronal plane as the two lower front teeth, and a flexible component (or "flexible member") 13, which may extend from at attachment point 21 at the bottom (or "caudal") end of the extension component 12 further caudally and may allow a patient to provide traction on the device 5. The flexible component 13 may be attached at its caudal end to a handle or ring 14, which the patient may grip during use. The tooth piece 9 may fit over one or more lower teeth and includes a channel 10 with lips 11 on each side of the channel 10. The extension component 12 may include a chin pad 20 and may have a wide variety of lengths, shapes and sizes. For example, the extension component may have an overall length of between about 2 inches and about 24 inches.

Figure 1B:
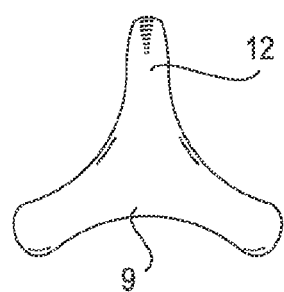

FIG. 1B is a top view of the device 5 and demonstrates the tooth component 9, which fits over the teeth, and the upper part of the extension element 12.

Figure 1C:
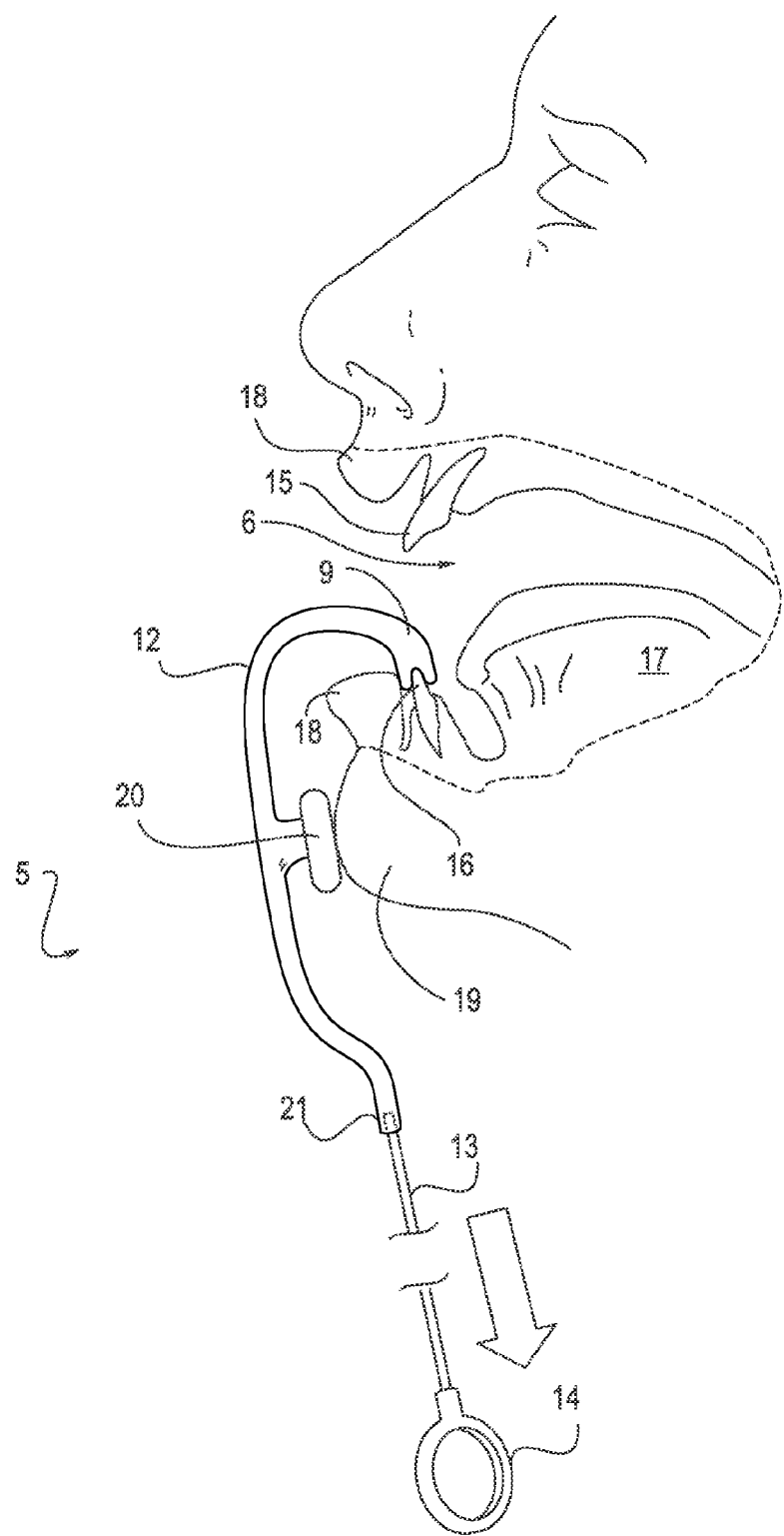
FIGS. 1C and 1D are side/cross-sectional and perspective views, respectfully, of a mouth, illustrating operation of the mouth opening device of FIGS. 1A and 1B, according to many embodiments.
Figure 1D:
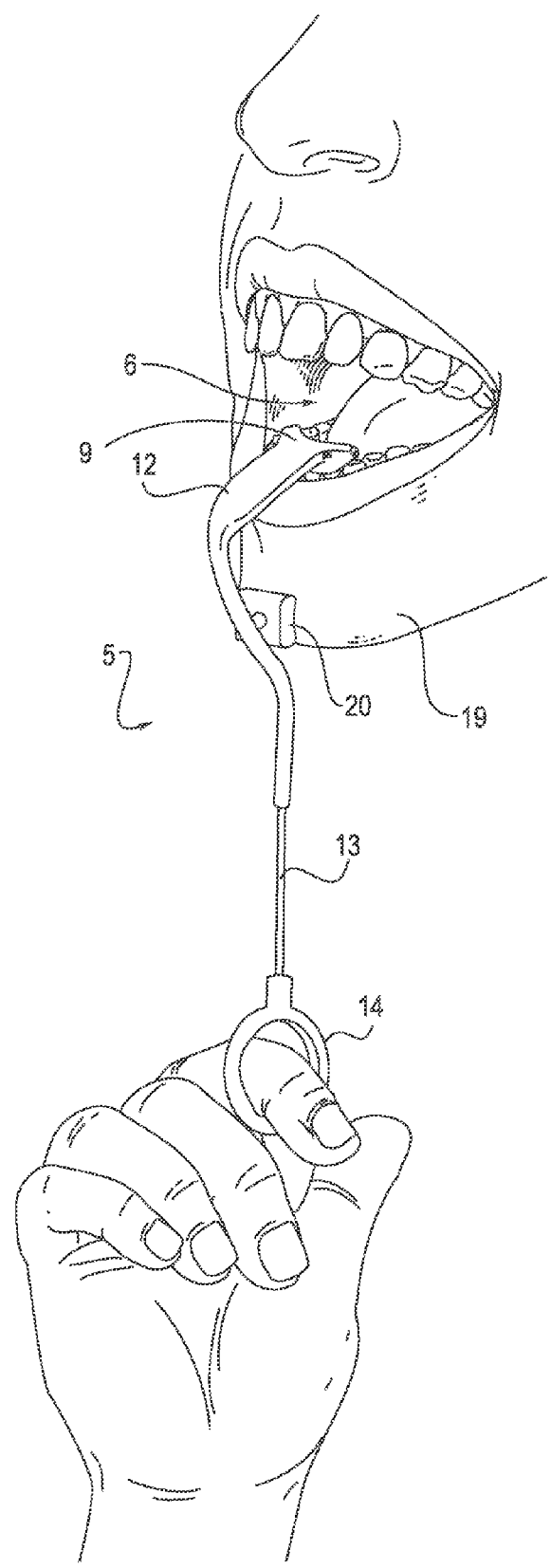

FIG. 1C is a midline cross-sectional view of a mouth 6, showing an upper tooth 15, a lower tooth 16, the tongue 17, the lips 18 and the chin 19. FIG. 1C illustrates how the tooth component 9 may rest over the lower tooth 16, with the chin pad 20 resting against the chin 19. Pulling the handle/ring 14 downward may cause the mouth to open and the chin 19 to lower relative to the skull and upper mouth. FIG. 1D is a perspective view of the mouth 6 and device 5 from FIGS. 1A-1C.

As illustrated in FIGS. 1C and 1D, the device 5 may be used for deflection of the jaw or chin 19. The chin pad 20 may be included or not included. Pulling downward on the jaw can stimulate a reflex that relaxes the closing muscles of the jaw, so the action of the device can not only aid the opening muscles, but can also relax the opposing closing muscles. By combining the assistance to the small opening muscles with traction and relaxing the large opposing closing muscles at the same time, the patient may be able to comfortably maintain an open mouth for a protracted period of time.

It may be important that the direction of the traction be in the longitudinal axis of the teeth, as they may be subjected to this same force daily during chewing and other activities. They may be accustomed to this direction of force. Traction anteriorly or obliquely forward may cause a tilt of the tooth and may loosen them. Any force directed other than along the long axis of the engaged teeth may be expected to displace the teeth and loosen them, especially if that force was exerted for 30 minutes or longer. The devices described herein may be designed so that the direction of force is along the vertical axis of the teeth, hence avoiding this potential problem. Additionally, traction outward or from posterior to anterior may create forces detrimental to the temporomandibular joint (TMJ). The device 5 may be designed so that the direction of force is along the vertical axis of the teeth, hence avoiding this potential problem. This direction of force is best illustrated in FIG. 1C and in FIG. 2 described below.

Figure 2:
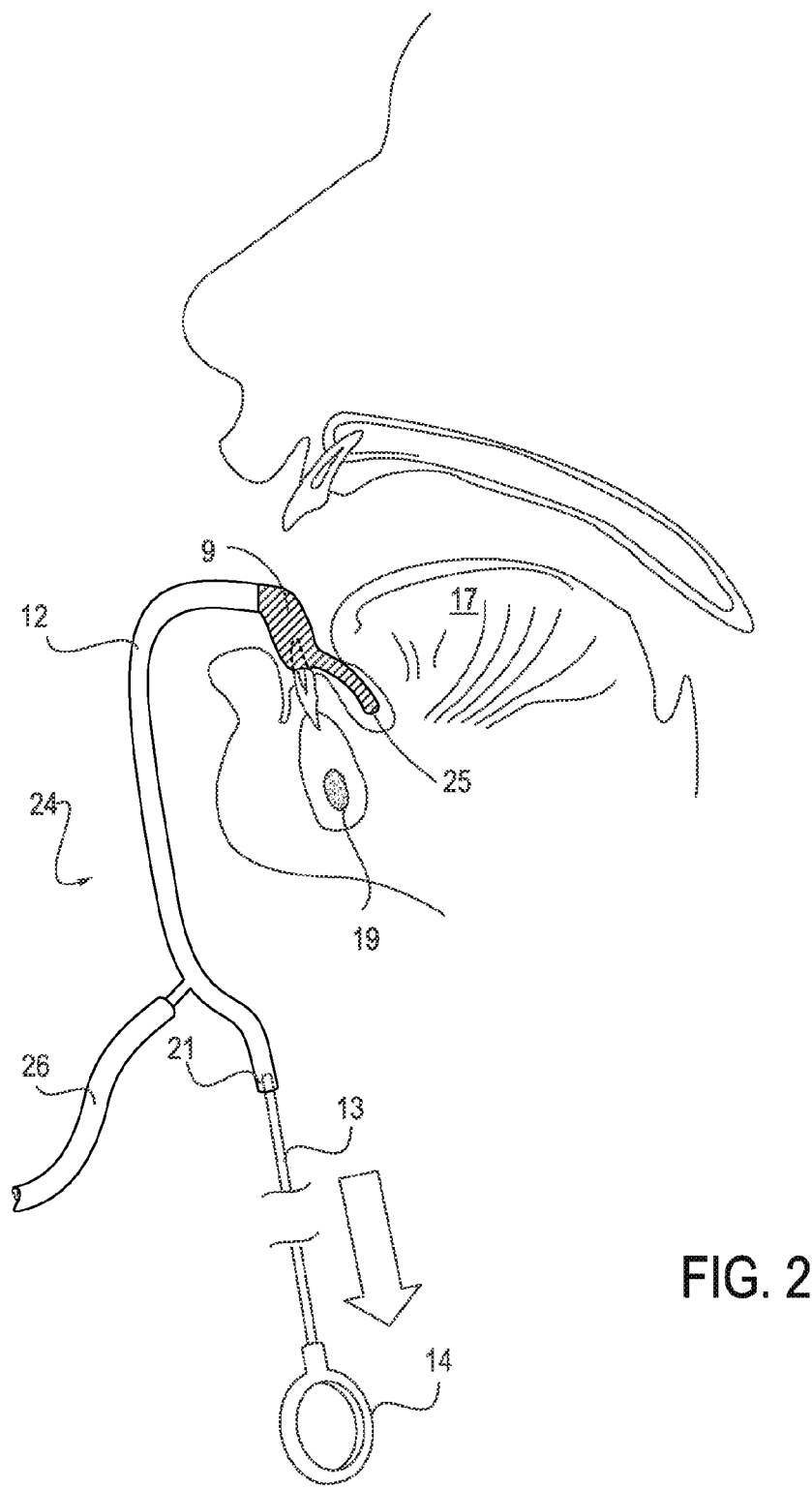
FIG. 2 is a sagittal view of a mouth and a side view of a mouth opening device in position in the mouth, according to many embodiments.

Referring now to FIG. 2, a sagittal view of the mouth is shown, along with a mouth opening device 24. The attaching component 9, extension element 12, flexible component 13 and ring 14 of the mouth opening device 24 may be the same or similar to the corresponding components of the mouth opening device 5 and other mouth opening devices described herein. A difference may be that the extension element 12 of the mouth opening device 24 does not include a chin pad. The device 24 may also include a suction channel within the extension element 13 and attaching component 9. A suction extension 25 may extend from the attaching component 9 to a point under the tongue 17 where most of the saliva exits the salivary ducts. There may also be a suction tubing 26, attached to the extension member 12 on one end and available suction machine on the other end. This combination of comfortable distraction of the jaw 19 and suction of saliva can be appealing for several reasons, one of which is that it may obviate the need for recurrent interruptions of the procedure to aspirate saliva from the mouth. It may even obviate the need for a dental assistant.

With reference now to FIGS. 3A-3D, a mouth opening device 28 is shown, which may not include the flexible member of the mouth opening devices 5 and 24 described above. Otherwise, the components of the mouth opening device 28 may be the same or similar in many respects to that of the other mouth opening devices described herein and vice versa. The device 28 may include a tooth piece component 30, which may fit over at least one lower tooth, an inflexible extension component 32 (or "handle"), which may extend out of the mouth and over the lower lip extending caudally to a point under the chin to a point approximately in the same coronal plane as the two lower front teeth, and a gripping member 33 (or "finger loop") for gripping and applying downward traction by the patient. The gripping member 33 may be a finger hole, but any other types, sizes and configurations of gripping portions may also be used. The tooth piece 30 may be made of a softer durometer material, formed into small posts 31, which may form the small groove 34 to accommodate the teeth and provide stability. The posts 31 may be arranged so that the teeth may fit between them, either side to side or front to back, so that the device 28 may be used either in the midline of the patient, i.e., directly over then under the chin, or from the side of the mouth, i.e., ninety degrees from the midline position. This latter position may place the curve of the handle 32 out of the way of the dental practitioner. Moreover, the posts 31 may be supplanted or augmented by deeper grooves (not shown) to receive the teeth. These grooves may be oriented transversely within the tooth piece 30 so that the device 28 may be positioned directly in the midline and in an anterior posterior or sagittal direction within the tooth piece 30, so that the device 28 may be positioned over the front teeth ninety degrees from midline. The device 28 may comprise either of the transverse or sagittal grooves or both and may be used from directly in the midline to the side of the mouth.

The handle 32 is typically relatively solid and inflexible. The handle 32 can add stability to the device 28 and may help ensure that the direction of the force applied by the patient is in the long axis of the tooth. The finger loop 33 of the handle 32 may be directly beneath the tooth, whether the handle 32 and device 28 are positioned in the midline or ninety degrees from midline, so the direction of force applied by the patient is generally with the long axis of the tooth. Any traction not in the long axis of the tooth may tilt and loosen the teeth and potentially damage the TMJ, especially when traction is applied for 30-60 minutes, the usual length of most dental procedures.

Moreover, the inflexible handle 32 may allow the patient to adjust the tooth piece 30 from the finger hold 33, which may be difficult or impossible with embodiments that include a flexible member. The patient may also be able to control the tooth piece 30 when closing the mouth at certain intervals to rest and to maintain its position with the teeth. Maintaining the position on the teeth would be extremely difficult with a flexible connection between the hand hold means and the tooth piece, especially without any accessory attachment means to the teeth similar to the grooves or posts previously discussed.

Figure 3A:
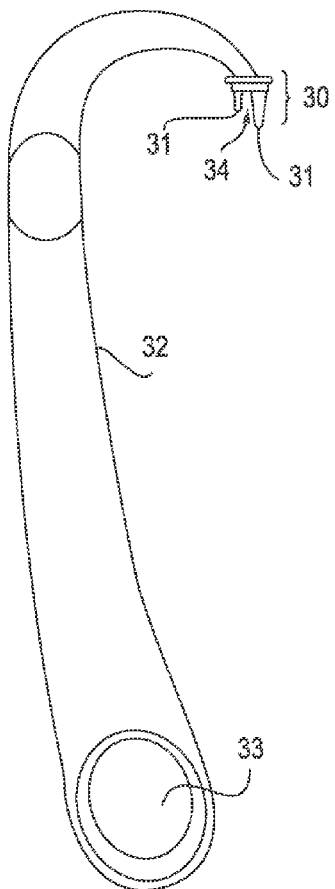
FIGS. 3A-3C are side, front and bottom views, respectively, of a mouth opening device, according to many embodiments.

As best illustrated in FIG. 3A, the tooth piece component 30, which fits over the lower teeth, may include a channel 34 with posts 31 on either side. The inflexible extension component 32 may extend out of the mouth and over the lip (not shown) then downward to a point below the chin (not shown.) The lower or caudal portion of this extension component 32 may include (or alternatively may be attached to) the gripping member 33, which may be a handle, a handheld ring, or the like. The tooth piece or mouth piece 30 may be fairly rigid, so as not to slip off the perch on the lower teeth. This rigidity may be important in maintaining the relationship between the mouthpiece 30 and the teeth and in the ability to provide gradual and graded traction on the device 28, without it slipping off the teeth because of flexibility in the tooth piece. Flexibility may preclude the type of graded and gradual gentle pressure needed to accomplish maximum and comfortable mouth opening. The posts 31, or some other similarly functioning element to secure the tooth piece 30 to the teeth, may also provide the necessary stability for the device to function properly. For example, there may be times during a dental procedure when the dentist is not actively engaged in the mouth and changing tools or components that the patient may close or partially close the mouth. During this action of closing the mouth, the tooth piece 30 may become dislodged or malpositioned, if there were no means on the tooth piece 30 to secure it, especially if there was a flexible connection. The flexible connection would preclude control of the tooth piece 30 by the patient and the ability of the patient to adjust the position of the tooth piece 30 at all.

In addition, the device may have a tensiometer interposed between the extension component 32 and the gripping member 33, so that when downward traction is provided by the patient, the tensiometer displays the force. This display may encourage the patient to provide more or less traction by emitting different audible sounds if the tension provided by the patient was more or less than desired. This tensiometer-based alarm may be an important safety feature, which may optimize the opening of the mouth while preventing damage to the temporomandibular joint and other tissues. The tensiometer may be releasably attached to the gripping member 33 or some other point on the handle mechanism, and another traction point or finger hole may be provided from which to provide traction. As well, the tensiometer may be provided separately for employment with any of the mouth opening devices described herein. It may be attached to the component, which extends out of the mouth, a handle, or the gripping member 33 in one of any number of ways.

Figure 3B:
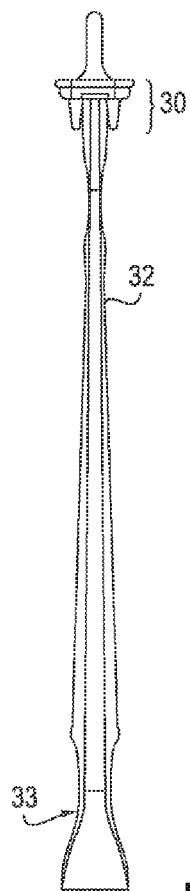

FIG. 3B is a front view of the mouth opening device 28, illustrating its thin profile. The thin design may occupy less space than thicker design while maintaining strength necessary to accomplish the necessary tasks. The tooth piece 30 may contain a swivel mechanism at the connection to the handle so that the tooth piece can be turned in relationship to the handle so that the handle can be positioned at virtually any position from one side of the mouth to the other.

Figure 3C:
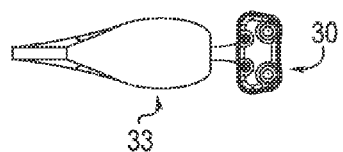

FIG. 3C is a bottom-up view of the device 28, slightly tilted to demonstrate the finger loop 33 is directly beneath the tooth piece 30.

Figure 3D:
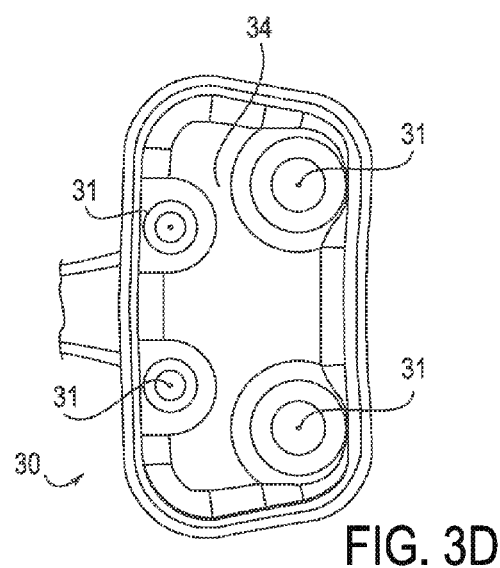
FIG. 3D is a close-up, bottom view of a tooth piece of the device of FIGS. 3A-3C.

FIG. 3D is a bottom view of the tooth piece 30, demonstrating the position of the posts 31. This arrangement may allow the device 28 to be positioned in the midline or ninety degrees from midline while still positioning the finger loop 33 directly under the front teeth and allowing the downward traction to be along the long axis of the teeth.

Figure 4:
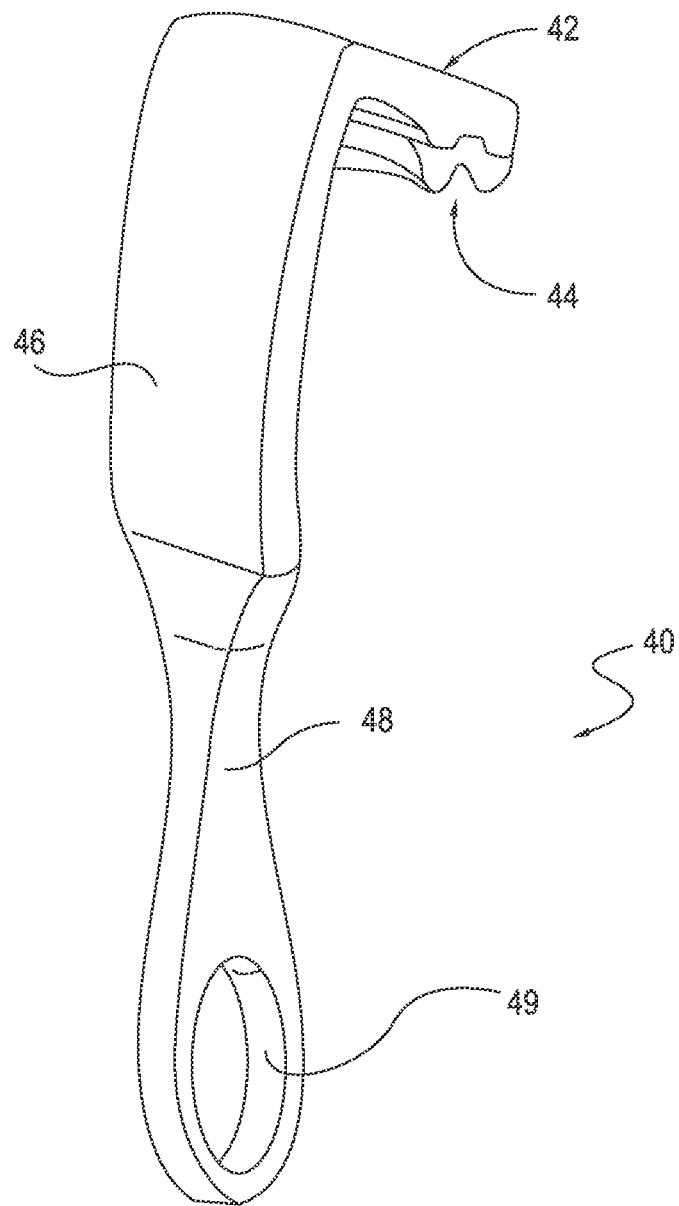
FIG. 4 is a posterior perspective view of a mouth opening device, according to many embodiments.

FIG. 4 is a posterior perspective view of a mouth opening device 40. The components of the mouth opening device 40 may be the same or similar in many respects to that of the other mouth opening devices described herein and vice versa. The device 40 may include a tooth engaging portion 42, which may include a soft, tooth-contacting surface 44, a neck portion 46 and a handle 48, which may include a finger hole 49. The top or apex of the neck portion 46 may not protrude as far cephalically in some of the other mouth opening devices described herein.

Figure 5:
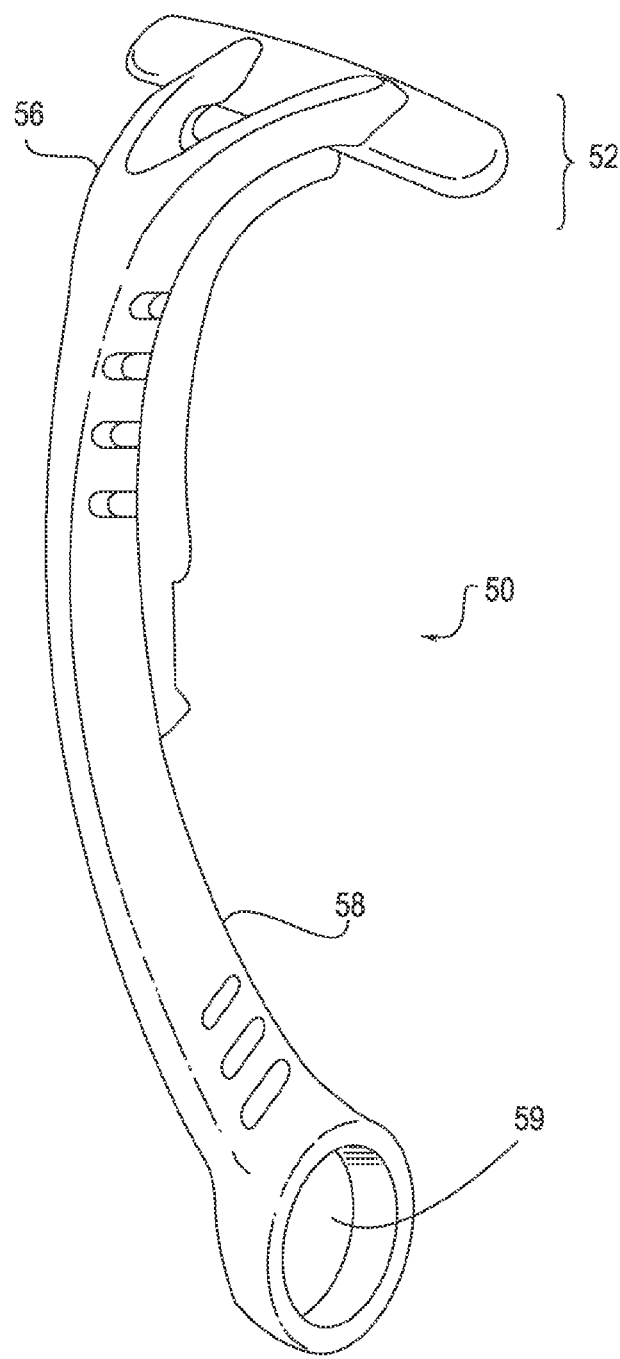
FIG. 5 is a posterior perspective view of a mouth opening device, according to many embodiments.

FIG. 5 is a perspective view of a mouth opening device 50, which may include a tooth engaging portion 52, a neck portion 56, and a handle 58 with a finger hole 59. The components of the mouth opening device 50 may be the same or similar in many respects to the other mouth opening devices described herein and vice versa. The tooth piece 52 may include any of the tooth-engaging components described herein, such as the posts and troughs described herein. As well, because of their low profile design, the more cephalic aspect of the handle may provide a finger rest for the dentist to assist in stability of the dental devices and hands and fingers within the mouth. The direction of force may be with the long axis of the teeth.

Figure 6A:
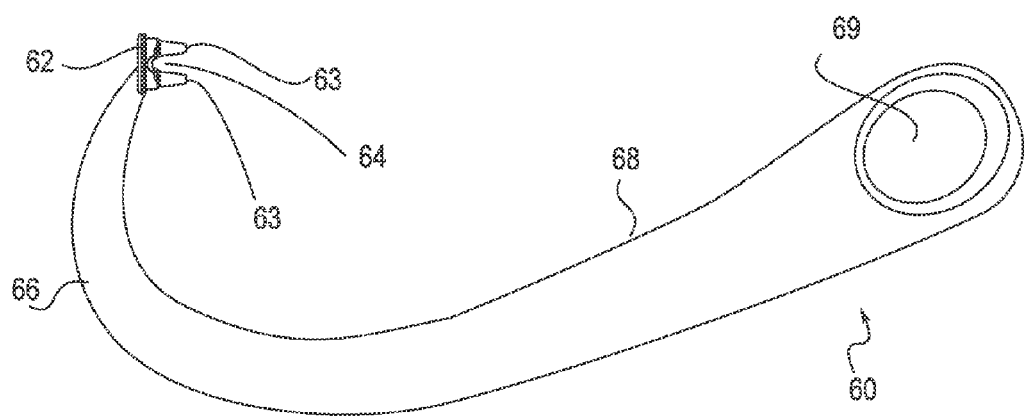
FIGS. 6A-6C are side, close-up/front and close-up/side views, respectively, of a mouth opening device, according to many embodiments.
Figure 6B:
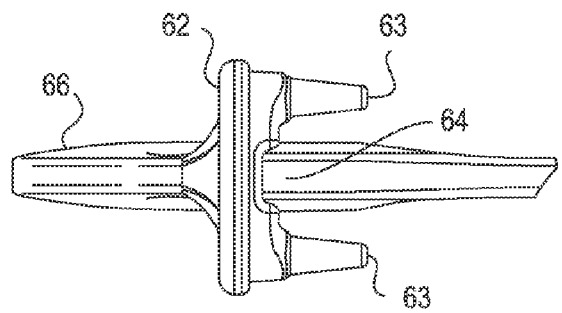
Figure 6C:
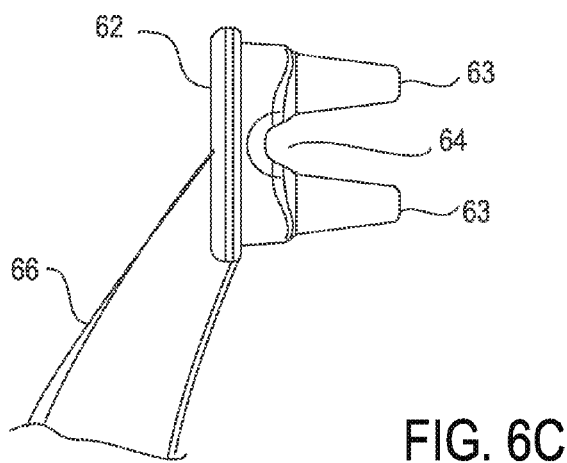

FIGS. 6A-6C are side, close-up front and close-up side views, respectively, of a mouth opening device 60. The components of the mouth opening device 60 may be the same or similar in many respects to that of the other mouth opening devices described herein and vice versa. The device 60 may include a tooth engaging portion 62, a neck portion 66, and a handle 68, which includes a finger hole 69. The tooth engaging portion 62 includes multiple posts 63, which are typically made of a softer material than the rest of the device 60, and which form a bidirectional trough 64 (or "groove"). The apex of the neck portion 66 may be less prominent, projecting not as far cephalically as in the mouth opening device 5 described above. The curvature of the handle neck portion 66 and handle 68 may be exaggerated compared to that in the mouth opening device 5 described above, which may provide additional room for the mandibular body and associated soft tissues within the curvature, so the device 60 can be placed ninety degrees from midline while still engaging the middle front teeth. The distance from the front teeth to the side of the jaw may be greater than the distance from the front teeth to the mental protuberance or chin, which may be appropriate for the device 60 if used from the side while the tooth piece is engaged over the lower middle front teeth. This aspect of the construction of the device gives the device 60 may give more utility than device which must be applied and used only from a midline position as it positions the device 60 to one side and out of the dentist's way.

FIGS. 6B and 6C are close-up views of the tooth piece 62, demonstrating the combination of the shallow groove 64 and posts 63 that may accommodate the front teeth from a midline position or ninety degrees from midline. A groove alone may not accommodate all different configurations of lower front teeth and different sized mandibular arches that occur in the general population. The variations in anatomy may demand different sized and shaped grooves if the tooth piece was constructed only with a groove or trough to engage the teeth. The combination of the groove 64 with the posts 63 will provide the stability and secure engagement necessary for the device to provide adequate downward fraction without slippage. The tooth piece 62 may also be constructed with a soft durometer material, at least in the trough or groove 64, which may allow the teeth to indent that material when engaging the device, creating traction and more stability than would be present if the material was not soft and compressible. Hence, the tooth piece 62 may comprise at least one or a combination of the following: one or more grooves 64 or troughs to receive the teeth, posts 64 or other means to receive the teeth, and a softer durometer material at the base.

Figures 7A, 7B, 7C:
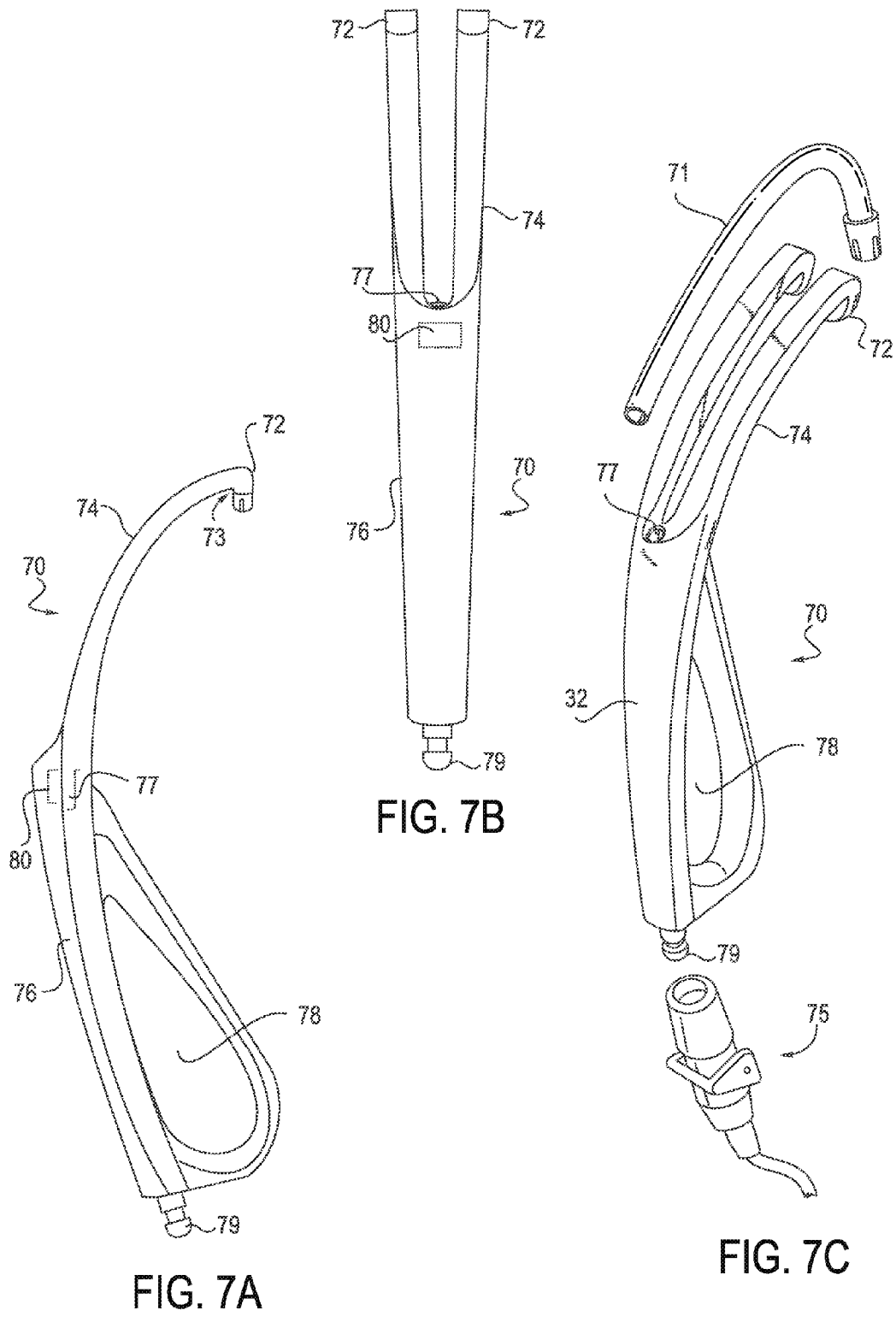
FIGS. 7A-7C are side, front and posterior perspective views, respectively, of a mouth opening device with components for connecting with a suction device, according to many embodiments.

Referring now to FIGS. 7A-7C, a mouth opening device 70 may include suctioning component(s) to provide suction through the device 70. The components of the mouth opening device 70 may be the same or similar in many respects to that of the other mouth opening devices described herein and vice versa. This combination of comfortable distraction of the jaw and suction of saliva may obviate the need for recurrent interruptions of the procedure to aspirate saliva from the mouth. In some procedures, it may even obviate the need for a dental assistant. It generally will make it simpler for the patient to hold onto only one item.

Suction or evacuation may be provided by either attaching a standard or modified suction device to one of the mouth opening devices described herein, or alternatively or in combination, may be provided via a built-in suction channel within a handle of the device. The device 70 may include a tooth engaging portion 72 with an angled section 73, a neck portion 74, a handle 76, which may include a hand hold 78, a suction channel 77 in the handle 76, and a suction connector 79 at the caudal end of the handle 76. As illustrated in FIG. 7C, a piece of suction tubing 71 may be connected to one end of the suction channel 77, and a source of suction force 75 may be attached to the suction connector 79, in order to provide suction within the mouth during a procedure.

FIGS. 7A-7C illustrate a mouth opening device 70 that includes a suction component. The tooth engaging portion 72 (or "tooth piece") may be configured as a rounded hook and includes a sharp corner 73, to engage the lower front teeth, instead of the posts and grooves described earlier. Alternatively or in combination, the posts and grooves may be employed in the mouth opening device 70. The neck portion 74 extends from the tooth engaging portion 72, and the handle 76 with the hand hold 78 extends from the neck portion 74. As illustrated in FIGS. 7B and 7C, the tooth engaging portion 72 and the neck portion 74 may be forked, so that each portion has two halve or prongs. The suction channel 77 in the handle 76 may extend from a suction tubing recess 80 at one end to the suction connector 79 at the other end.

FIG. 7B is a frontal view of the device 70, which demonstrates the forked neck portion 74 and tooth engaging portion 72. Between them may be a space for the suction tubing. At the junction of the neck portion 74 with the handle 76, the suction tubing recess 80 may be configured to receive a proximal end of a piece of suction tubing 71, preferably with a friction fit. It may comprise an O ring or other means to secure within the cavity or recess 80. Alternatively or in combination, a ribbed connector may be used instead of the cavity or recess 80.

FIG. 7C is an oblique perspective view of the device 70, which illustrates how a standard suction tube 71 may be inserted into the cavity or recess 80, so that the tip of the suction tube fits over the front teeth adjacent to the tooth pieces 72. With the suction tube 71 in place and the caudal end of the device connected to a suction hose 75, the suction tube 71 is stabilized, while downward traction can be provided by the patient.

Figure 8C:
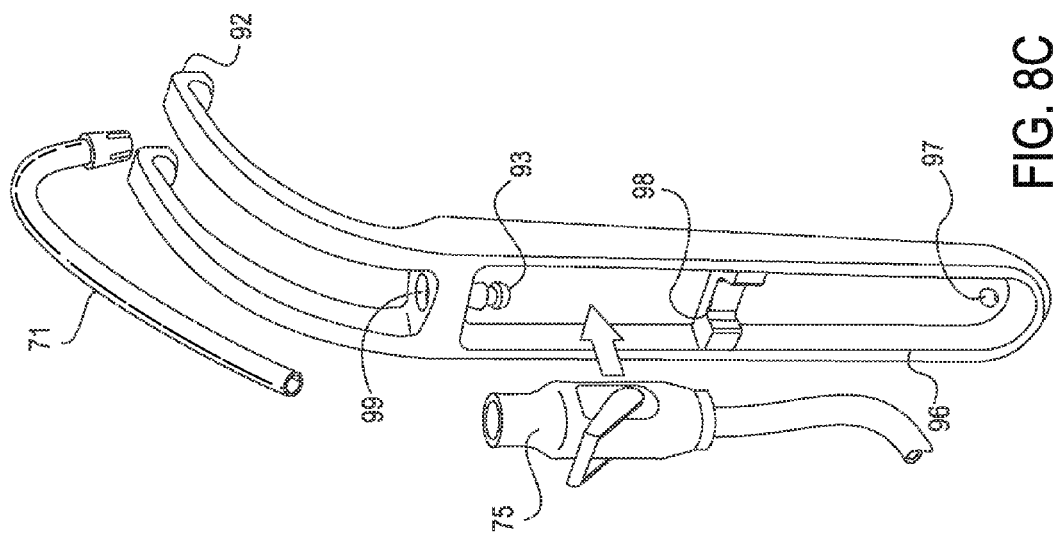
FIGS. 8A-8C are side, front and posterior perspective views, respectively, of a mouth opening device with components for connecting with a suction device, according to many embodiments.
Figure 8B:
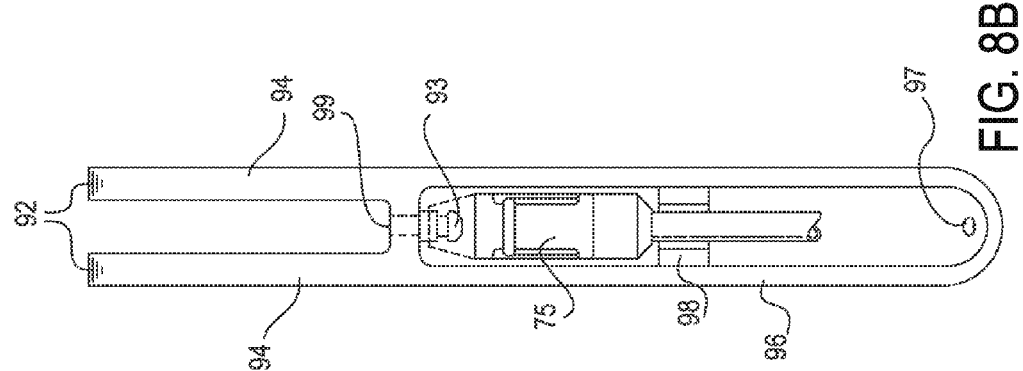
Figure 8A:
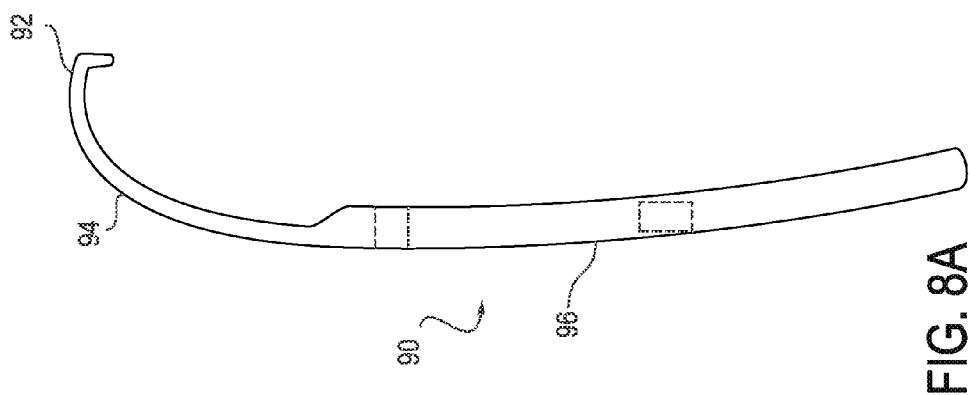

FIGS. 8A-8C are side, front, and rear perspective views, respectively, of a mouth opening device 90. The components of the mouth opening device 90 may be the same or similar in many respects to that of the other mouth opening devices described herein and vice versa. The device 90 may include a tooth engaging portion 92, a neck portion 94 and a handle 96. The tooth engaging portion 92 is forked and has a sharp corner to secure the teeth and a very low profile overall. The neck 94 may also be forked. The device 90 may also include a suction tube recess 99 and a suction valve connector 93, which are configured to attach to suction tubing 71 and a suction hose 75, respectively. The handle 96 may include a tube rest 98 for supporting the suction hose 75 and a finger hold 97 for facilitating holding of the handle 96 by the patient.

FIG. 8C is an oblique perspective view of the device 90, with the suction tube 71 and suction hose 75 detached. Standard suction tubes and standard suction valves that are commercially available may be used with any of these embodiments. Alternatively or in combination, specialized tubes and connectors may be used with any of the mouth opening devices described herein.

Referring now to FIGS. 9A-9E, a mouth opening device 100 may provide suction without the use of an additional suction tubing piece. The components of the mouth opening device 100 may be the same or similar in many respects as the other mouth opening devices described herein and vice versa. The device 100 may include a tooth engaging portion 102, a neck portion 104, and a handle 106, which includes a hand hold 107 and a suction connector. As illustrated in the cross-sectional drawing of FIG. 9D, the handle 106 and the neck portion 104 may both be hollow, thus forming a suction channel 110, which extends from the tooth piece 102 to the suction connector 108. As illustrated in FIG. 9C, suction inlets 112 into the suction channel 110 may be located along one or more sides of the tooth engagement portion 102. The suction inlets 53 may even extend even further toward the gingival margin 114 than is indicated in this illustration, even curving under and abutting the gingival margin 114 in some cases. With this configuration, the device 100 can help evacuate the mouth of saliva, if the patient closes his/her lips about the distal aspect of the device 100.

Referring to the tooth piece 102, it may be desirable that the tooth piece 102 extend as far toward the gingival margin as possible so that suction is optimized, but without contacting or impinging on the gums or gingiva. This could range from 3 to 15 mm, but optimally may be 6-9 mm. Since the suction inlets 112 may not extend to the dependent portion of the mouth where saliva and fluids collect, the mouth may be closed and the lips pursed around the neck portion 104 to evacuate fluid from these dependent portions of the mouth. In this position, with the lips closed around the neck portion 104, air may travel through the nostrils, the nasopharynx, and the oropharynx and out through the suction inlets 112, and, in the process, will evacuate fluid and saliva that may be pooled in the dependent portions of the mouth.

Alternatively or in combination, the inflexible one-piece construction of the handle 106, the neck portion 104 and the tooth piece 102 may allow the device to be tilted upward by elevating the handle 106 so that the tooth piece can be directed into dependent portions of the mouth by the patient or the dental practitioner to directly aspirate and evacuate fluid and saliva. A compact tooth piece 102 may allow the positioning the suction inlets 112 in a variety of areas within the mouth that would not be practical if the tooth piece 112 were larger. Moreover, without the inelastic, inflexible neck portion 104, this maneuver may not be possible. As well, the surface of the neck portion 104 which abuts the upper and lower lips may be smooth for this maneuver to be practical as the device may be more or less inserted into the mouth. Irregularities or sharp corners could irritate or even lacerate the lips during this maneuver.

Alternatively or in combination, a simple attachment mechanism may be provided on the handle proximal to the tooth piece to releasably or fixably attach the suction component and the attachment mechanism may be one or more of metal, rubber, plastic, polymer, fabric, fiber or adhesive or the like. Moreover, the intraoral suction component the mouth opening devices may be positioned so that there is tubing or other similarly function element to provide suction that may be placed over the front teeth or, alternatively or in combination, along the labial or front side of the teeth and circle dorsally around the molars so that the tip of the suction component is positioned on the lingual or back side of the lower front teeth. This portion of either suction component may also comprise a component which serves to displace at the cheek and/or the tongue away from the area in which the dentist intends to work. In other words, a displacement component may be combined with the suction component and may be placed either over the lower front teeth or along the labial or front side of the teeth and then around the molars so that it provides both suction and displacement. This displacement of the tissues may usually be away from the ipsilateral side occupied by the suction component. The displacing component of this displacing suction component may be tubular, flat, or any other shape which provides both suction and displacement and may provide such functions in a relatively low profile. This may provide exposure for the dental practitioner and keep the moist tissues of the cheek and tongue away from the area being treated.

Figure 10:
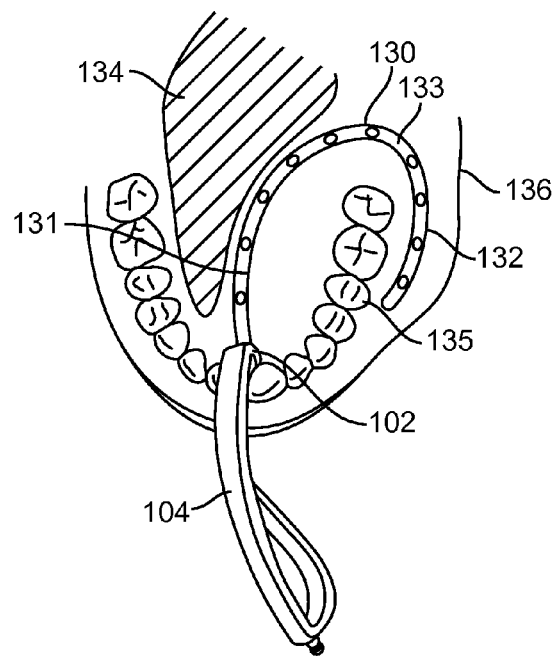
FIG. 10 is a top down perspective of the lower mouth with a mouth opening device, according to many embodiments.

An example of the device is shown in FIG. 10. The displacement mechanism is shown as attached to the device 90, for example, but it may be attached, affixed to or connected to any device which distracts the jaw downward and provides suction. In the devices in which the suction/distraction component is placed over the lower front teeth, as shown in FIG. 10, the suction/distraction component 130 may comprise a lingual component 131 adjacent to and displacing the tongue 134 and a labial component 132 which may be placed between the teeth 135 and the cheek 136 and may displace the cheek 136 away from the teeth 135.

The position of the suction and the displacing means may vary, depending on whether the device is placed so that it exits the mouth midline or on the right or left side and whether the side in which the device is placed is the ipsilateral or contralateral side of the mouth in which the dentist is working. Hence, multiple different configurations of the suction and displacement components are likely, as well as the attachment component to the suction and whether the suction is integral within the handle or a separate tubing, which may be attached to the device and on which side it is attached or connected to the handle.

Figure 11:
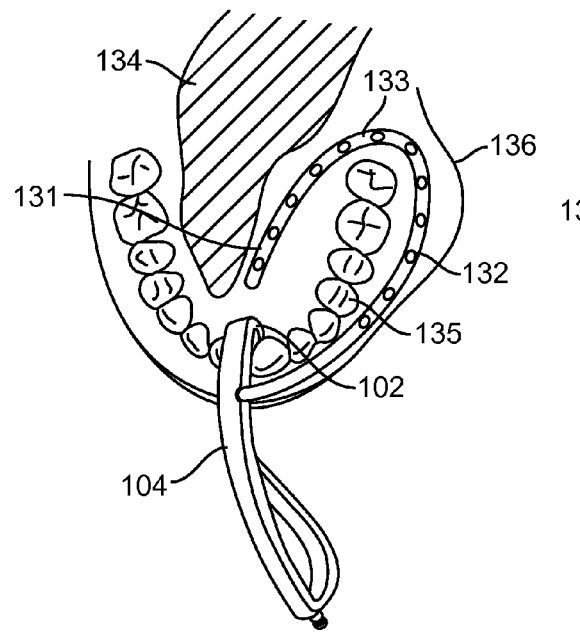
FIG. 11 is a top down perspective of the lower mouth with a mouth opening device, according to many embodiments.

In FIG. 11, the suction/displacement component 130 is attached to the distal aspect of the neck 104 of the traction device preferably on either side, but also possibly underneath or over the distal neck 104. The labial component 132 may comprise the proximal portion of the suction/displacement component 130 and may displace the cheek 136 while providing suction in that region. The lingual component 131 may comprise the distal portion and may provide displacement of the tongue 134 and suction in the floor of the mouth. Both may be tubular structures as illustrated with holes 138 to allow the fluids to enter and be removed.

Figure 12:
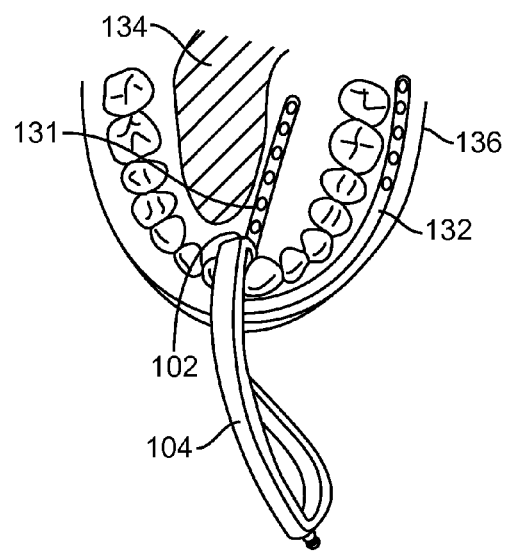
FIG. 12 is a top down perspective of the lower mouth with a mouth opening device, according to many embodiments.

In FIG. 12, the lingual portion 131 of the suction/displacement component 130 may originate from the tooth engaging portion 102 of the mouth opening device and the labial component 132 may originate from the distal neck 104 of the mouth opening device. The suction/displacement component 130 may be fixed to or releasably attached to the tooth engaging portion 102 or the handle 104 of the device in any number of ways, and the components may be attached to any of the different elements of the mouth opening devices described.

Figure 13:
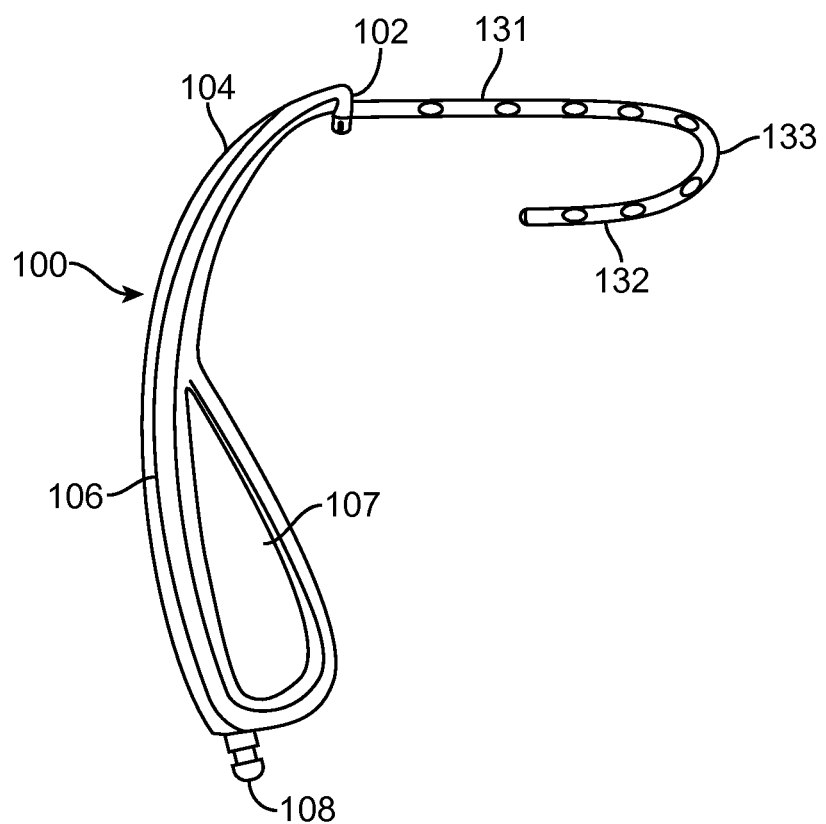
FIGS. 13-15 are side perspectives of mouth opening devices, according to many embodiments.

In FIG. 13, the proximal portion of the suction/displacement component 130 is shown as attached to the tooth engaging portion 104, the lingual portion 131 being proximally positioned and the labial component 132 positioned distally.

Figure 14:
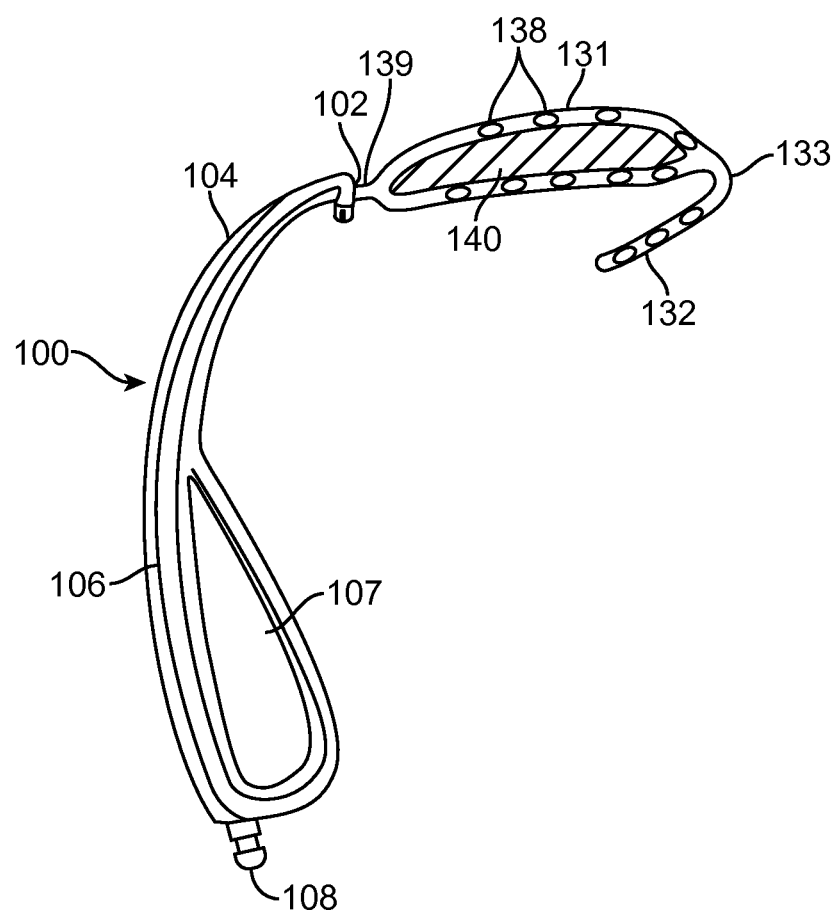

FIG. 14 demonstrates a similar configuration as FIG. 13, but the lingual component 131 may be wider than just a tubular structure. The lingual component 131 may comprise two tubes with holes 138 and a membrane 140 between the two tubes to keep them spatially separated. The membrane may be plastic or any one of a number of materials. Smaller tubes may even extend into the membrane 140 to provide additional suction to the lingual 131 and labial portions 132. Point 133 may be where the device wraps around the posterior molar and where the lingual portion 132 is directed forward in this and other embodiments herein. As shown, the membrane 140 is between the tubular structures, but it may extend beyond the margins of the tubular structures from 1 mm to 3 cm. Moreover, the membrane 140 may be constructed of or comprise a reflective material to enhance the available light within the mouth.

Figure 15:
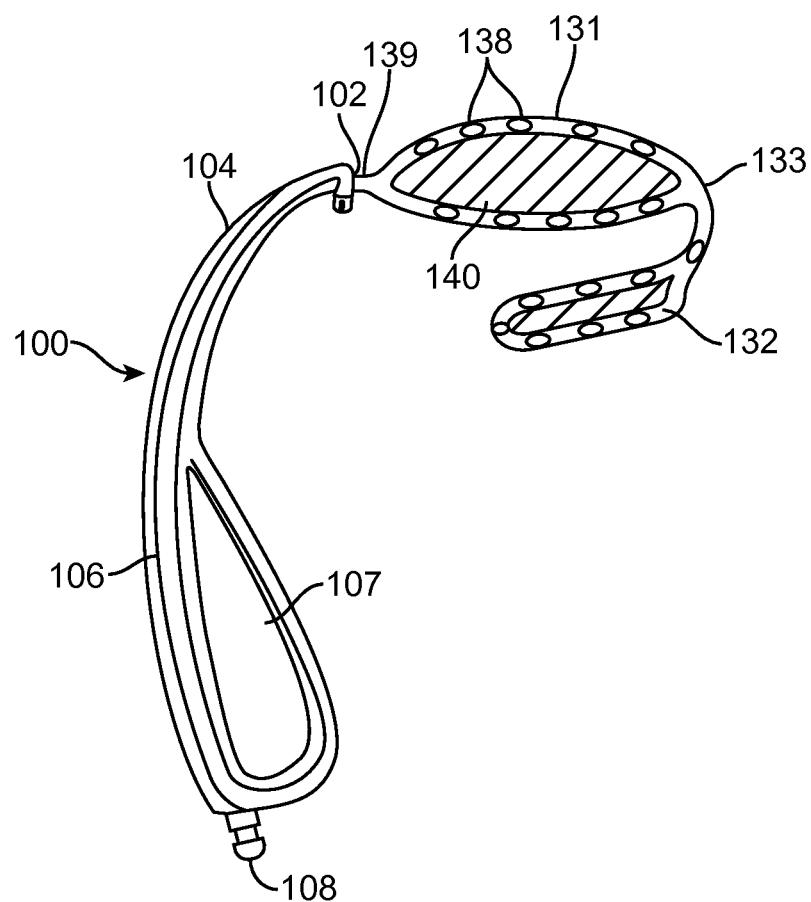

FIG. 15 demonstrates a configuration similar to that shown in FIG. 14, but the labial portion 132 may be a double tubular structure with a membrane 140 between the tubular structures. The point 133 may be a singular structure as shown to facilitate the curve around the posterior molars, but may be a double tubular or other structure (not shown) as well.

Figure 16:
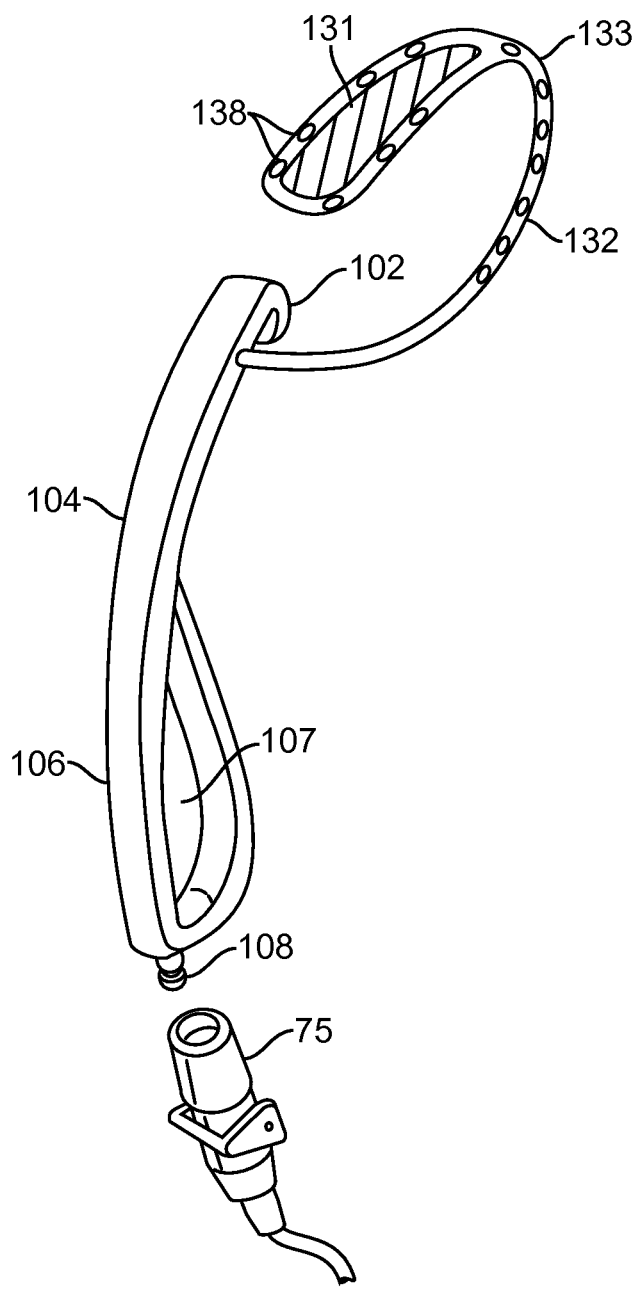
FIG. 16 is an oblique perspective of the device of FIG. 11.

FIG. 16 is a perspective of a mouth opening device configured similarly to that shown by FIG. 11. The labial component 132 is proximal and the lingual component 131 may be distal. It may be attached to any one of a number of points of the distal neck 104 of the device. Here it is attached to the side. The labial component 132 may displace the cheek and the lingual portion may displace the tongue.

The construction of suction/displacement component 130 may utilize any one of a number of materials including plastic, silicone, polyethylene, C-Flex, polyurethane, Chonoprene amongst others. A material of a durometer that maintains some stiffness, but may be flexible enough to be comfortable may be used. In the one piece configuration, it may be generally horse shoe shaped and may have a relatively low profile area 133 in the turn between the lingual 131 and labial 132 portions.

As illustrated above, suction can be provided in a number of configurations, and thus, the described are merely examples of some of the configurations. Suction may be provided by just the suction tube, suction valve, and suction hose, or by providing connections between some of these suction components. The suction components also may attach to the elements of a device, to stabilize the suction apparatus. The elements of a device may stabilize the suction components by cradling the suction components, for example, rather than being connected or attached to them.

Experimental Examples

In using the above, the tooth piece may be placed over the lower front teeth by the dental practitioner or the patient, and the patient may secure the handheld apparatus. To maximize the effectiveness, the patient can place downward pressure on the device and the mandible while consciously urging the mandible upward. This may be a strain against the downward force. The patient may then relax and stretch the muscles with continued downward force on the device. The patient may repeat this exercise one or more times, and then relax the jaw muscles and pull downward tension more or less continuously for a period of time. This method has, in a small trial, demonstrated a greater degree of measurable opening of the mouth with little or no discomfort more than any other method. During interludes when the dental practitioner is not occupied within the mouth, the patient may briefly rest by closing the mouth. Then downward traction or tension may be exerted on the device and mandible again and maximum opening achieved.

In testing this device and method, patients that actively opened the mouth without any assistance from any device lost an average of 10-25% of the original opening distance after 30 minutes in the procedure. Patients tested using a mouth opening device and method described above gained 10-30% of the original opening distance at the 30 minute period. The patients with the assist device and method were also more comfortable than patients without the assist device and method. Hence, the combination of the devices and methods described above benefited the dentist by providing significantly more exposure and the patient by obviating the pain usually experienced with this procedure.

In any of the devices described above, an added part or component may be provided to prop the mouth open. The devices of the present disclosure may be intended to keep the mouth open as described, but may not prevent the patient from closing the mouth unexpectedly because of a sudden pain or impulse to close. Abrupt closing could potentially displace a drill, burr, or other dental device and may cause damage to the instrument, the patient, and/or the dentist or dental practitioner. Ideally in at least some cases, this propping mechanism may not actually prop the mouth open, but may only serve to keep the mouth from closing significantly. In other words, it may function as a safety mechanism more than a means to keep the mouth open. The teeth may not abut this component, unless and until the patient unexpectedly closes the mouth. For example, the mechanism may simply comprise a material added to the cephalic aspect of the tooth piece or may be a separate component which is releasably or fixedly attached to the distal aspect of the handle adjacent to the tooth piece. Alternatively or in combination, these elements to prop open may be attached to the suction component or may be separate.

The devices described above may also be used in concert with other commonly used dental devices, including dental dams and other devices. One may combine the current device(s) with a displacement device that displaces the tongue and cheek away from the targeted teeth. This may be accomplished, for example, by modifying the suction component as described herein to accommodate the displacement device and suction. One may also combine the mouth opening devices described herein with a lip retractor configured to retract the lips to gain better exposure to the oral cavity.

Additionally, a light or means of illumination may be added to the handle, the tooth piece, the suction component, or the displacement component, or it may be provided separately and attached to any of the components above. Moreover, any of the components may be constructed of reflective material, which may serve to illuminate the teeth and oral cavity by reflecting light from the means of illumination described above or from some other source of light. Even further, any of the components, and especially the displacing component, may be constructed of material that glows or emanates light when that substance contacts moisture or glows or emanates light because of some other physical or chemical reaction. This process could be because of fluorescence, chemoluminescence, phosphorescence, light emitting diodes, or even organic light emitting diodes, among others. Any combination of light emitting substance and reflecting substance may be used.

The mouth opening device(s) described herein may also be made more visually attractive, which may be especially important when used in children. The mouth opening device(s) may comprise a detachable structure, a structure or attachment fixed to the device, or art applied to the device in one of several manners. While this visual component may represent an animate or inanimate object, one such structure may comprise a face or portions of a face that attaches to the neck to give the device a personality. This visual component may comprise one or more of eyes, mouth, ears, or nose and may represent an animal, person, plant, cartoon, or other figure. The visual component may be attached to, applied to, or incorporated into the neck or handle of the device. An exemplary visual component may be configured so that it may be removed from the device, preferably at the end of the procedure, and given to the patient. The visual component may be constructed so that it may be worn by the patient on clothing, in the hair, or even as a ring on a finger.

In maintaining a mouth of a patient in an open position during a dental procedure, methods of using the mouth opening device(s) described herein may comprise placing, by either the patient or the dental practitioner, a groove of a tooth engaging portion of a mouth distraction device over at least one lower tooth in a lower jaw of the patient's mouth and pulling down or providing traction on a handle of the mouth distraction device, preferably by the patient, to maintain the lower jaw in an open position relative to an upper jaw of the patient's mouth. This traction may be substantially continuous or intermittent. Suction may be provided by attaching a suction or vacuum source to or incorporating the suction or vacuum source within the distraction device. A tongue, cheek, or a tongue and cheek displacement element may be positioned by the dental practitioner to displace the tongue and/or cheek away from the area to be treated. A lip retraction element may also be positioned by the dental practitioner.

In at least some cases, optimally, the patient would provide downward traction on the mandible that would be sufficient to open the mouth as wide as possible while avoiding discomfort. The ideal balance of degree of distraction and the lack of discomfort can be achieved by the patient controlling the downward force of traction over the course of the procedure. The degree of distraction may be varied by the patient over the course of the procedure and may gradually increase as the initial traction causes the muscles of the jaw to relax. This variation may cause the jaw to open even more as the procedure progresses. The patient may intermittently close the mouth to relax, swallow or rest or may purse the lips about the neck of the device to evacuate the fluid within the mouth. Traction then may be reapplied by the patient to a degree that opens the mouth as wide as possible without generating discomfort. Repeating the traction, relaxation, and traction cycles may allow the mouth to open even further and without discomfort. By providing a handle that is rigidly affixed to the tooth engaging apparatus, the devices may maintain their relationship and prevent the tooth engaging portion from becoming displaced from the teeth when the patient closes the mouth to rest, relax, swallow, or evacuate fluid as may be the case with prior art devices. At the termination of the procedure, the device may be removed by the patient or the dental practitioner and properly disposed.

The devices described herein comprise different components and various configurations of these different components. The single or multiple configurations of the separate components may be combined with any single or multiple configuration of another component or components that may result in a device not explicitly described herein. By providing this flexibility in the structural configuration of various devices, the goals of providing the dental practitioner with greater exposure and convenience and the patient with greater comfort can be achieved.

Although the above description is complete and accurate, it is not meant to be exhaustive or to limit the scope of the invention beyond what is set forth in the following claims. Various alterations, modifications, additions, and deletions may be made to any of the devices and methods, without departing from the scope of the invention.

What is claimed is:

1. A device for helping maintain a mouth of a patient in an open position, the device comprising:
    a tooth engaging portion comprising at least one groove for accepting at least one lower tooth of the patient's lower jaw, wherein the at least one groove comprises a contact surface configured to contact a posterior surface of the at least one lower tooth when accepting the at least one tooth;
    an extension portion that extends away from the tooth engaging portion; and
    a rigid handle that extends down from the extension portion and ends in a caudal end that extends back toward the tooth engaging portion;
    wherein the caudal end of the handle is aligned with the contact surface of the at least one groove of the tooth engaging portion such that force from pulling the caudal end of the handle downward, when the tooth engaging portion is accepting the at least one lower tooth, is directed to the at least one lower tooth in a direction along the longitudinal axis of the at least one lower tooth, and
    wherein the handle and the extension portion comprise a solid, one-piece construct.

2. A device as in claim 1, wherein at least part of the tooth engaging portion comprises the solid, one-piece construct.

3. A device as in claim 2, wherein the tooth engaging portion comprises:
    a distal end of the solid, one-piece construct; and
    a piece of material attached to the distal end of the one-piece construct, wherein the piece of material is softer than the one-piece construct.

4. A device as in claim 1, wherein the extension portion is curved.

5. A device as in claim 1, wherein the extension portion and the tooth engaging portion are forked, and wherein a space between two prongs of the tooth engaging portion and the extension portion is configured to accept a suction tube.

6. A device as in claim 1, wherein the caudal end of the handle comprises a finger loop through which a finger of the patient or a medical professional may be extended to facilitate application of downward force.

7. A device as in claim 1, further comprising a suction member coupled with at least one of the tooth engaging portion or the extension portion.

8. A device as in claim 1, wherein at least one of the tooth engaging portion, extension portion, or handle comprise at least one suction channel.

9. A device as in claim 1, further comprising a tissue displacement member coupled with at least one of the tooth engaging portion or the extension portion, for displacing at least one of a cheek or a tongue of the patient.

10. A method of maintaining a mouth of a patient in an open position, the method comprising:
    placing a groove of a tooth engaging portion of a mouth distraction device over at least one lower tooth in a lower jaw of the patient's mouth so that a contact surface of the groove contacts a posterior surface of the at least one lower tooth;
    pulling down on a handle of the mouth distraction device to apply downward force on the at least one lower tooth to maintain the lower jaw in an open position relative to an upper jaw of the patient's mouth; and
    applying suction in the patient's mouth, using a suction device incorporated into or attached to the mouth distraction device,
    wherein pulling down on the handle of the mouth distraction device to apply the downward force comprises directing, with the mouth distraction device, the downward force to the at least one lower tooth in a direction along the longitudinal axis of the at least one lower tooth to distract the lower jaw.

11. A method as in claim 10, wherein the groove of the tooth engaging portion of the mouth distraction device is placed over the at least one lower tooth by at least one of the patient or a medical professional.

12. A method as in claim 10, wherein at least one of the patient or a medical professional pulls down on the handle of the mouth distraction device.

13. A method as in claim 10, further comprising, after the handle of the mouth distraction device is pulled:
releasing pulling force from the handle to allow the lower jaw to relax and the mouth to at least partially close; and
repeating pulling the handle of the mouth distraction device to reopen the mouth.

14. A method as in claim 10, wherein the placing the groove over at least one lower tooth comprises placing the groove over multiple lower front teeth.

15. A method as in claim 10, wherein at least one of the tooth engaging portion, extension portion, or handle comprise at least one suction channel.

16. A method as in claim 10, further comprising displacing at least one of a cheek or a tongue of the patient using a tissue displacement member incorporated into or attached to the mouth displacement device.

17. A method as in claim 10, further comprising, after the handle of the mouth distraction device is pulled:
passing a suction device through an opening in the mouth distraction device and into the patient's mouth; and
applying suction in the mouth with the suction device, while the distraction device maintains the mouth in an open position.

18. A device for helping maintain a mouth of a patient in an open position, the device comprising:
a tooth engaging portion comprising at least one groove for accepting at least one lower tooth of the patient's lower jaw, wherein the at least one groove comprises a contact surface configured to contact a posterior surface of the at least one lower tooth when accepting the at least one tooth;
an extension portion that extends away from the tooth engaging portion;
a rigid handle that extends down from the extension portion and ends in a caudal end that extends back toward the tooth engaging portion;
a tissue displacement member coupled to at least one of the tooth engaging portion, extension portion, or handle, the tissue displacement member being configured to displace at least one of a cheek or tongue of the patient when the at least one groove of the tooth engaging portion is accepting the at least one lower tooth; and
a suction tube coupled at least one of the tooth engaging portion, extension portion, handle, or tissue displacement member to provide suction to the patient's mouth,
wherein the tissue displacement member comprises a curved, tubular structure,
wherein the curved, tubular structure comprises a first tube and a second tube and a membrane therebetween, and
wherein the caudal end of the handle is aligned with the contact surface of the at least one groove of the tooth engaging portion such that force from pulling the caudal end of the handle downward, when the tooth engaging portion is accepting the at least one lower tooth, is directed to the at least one lower tooth in a direction along the longitudinal axis of the at least one lower tooth.

19. The device of claim 18, wherein the extension portion is curved.

20. The device of claim 18, wherein the extension portion and the tooth engaging portion are forked, and wherein a space between two prongs of the tooth engaging portion and the extension portion is configured to accept one or more of the suction tube or tissue displacement member.

21. The device of claim 18, wherein the caudal end of the handle comprises a finger loop through which a finger of the patient or a medical professional can be extended to facilitate application of downward force.

22. The device of claim 18, wherein the handle comprises a suction connector configured to connect to a suction source.

23. The device of claim 18, wherein the tissue displacement member is coupled to the suction tubing and comprises a tubular structure having at least one suction inlet port along a length thereof.

24. A device for helping maintain a mouth of a patient in an open position, the device comprising:
a tooth engaging portion comprising at least one groove for accepting at least one lower tooth of the patient's lower jaw, wherein the at least one groove comprises a contact surface configured to contact a posterior surface of the at least one lower tooth when accepting the at least one tooth;
an extension portion that extends away from the tooth engaging portion;
a rigid handle that extends down from the extension portion and ends in a caudal end that extends back toward the tooth engaging portion; and
a suction member coupled with at least one of the tooth engaging portion or the extension portion,
wherein the caudal end of the handle is aligned with the contact surface of the at least one groove of the tooth engaging portion such that force from pulling the caudal end of the handle downward, when the tooth engaging portion is accepting the at least one lower tooth, is directed to the at least one lower tooth in a direction along the longitudinal axis of the at least one lower tooth.

25. A device as in claim 24, wherein the handle and the extension portion comprise a solid, one-piece construct.

26. A device as in claim 25, wherein at least part of the tooth engaging portion comprises the solid, one-piece construct.

27. A device as in claim 26, wherein the tooth engaging portion comprises:
a distal end of the solid, one-piece construct; and
a piece of material attached to the distal end of the one-piece construct, wherein the piece of material is softer than the one-piece construct.

28. A device as in claim 24, wherein the extension portion is curved.

29. A device as in claim 24, wherein the extension portion and the tooth engaging portion are forked, and wherein a space between two prongs of the tooth engaging portion and the extension portion is configured to accept a suction tube.

30. A device as in claim 24, wherein the caudal end of the handle comprises a finger loop through which a finger of the patient or a medical professional may be extended to facilitate application of downward force.

31. A device as in claim 24, wherein at least one of the tooth engaging portion, extension portion, or handle comprise at least one suction channel.

32. A device as in claim 24, further comprising a tissue displacement member coupled with at least one of the tooth engaging portion or the extension portion, for displacing at least one of a cheek or a tongue of the patient.

33. A device for helping maintain a mouth of a patient in an open position, the device comprising:
- a tooth engaging portion comprising at least one groove for accepting at least one lower tooth of the patient's lower jaw, wherein the at least one groove comprises a contact surface configured to contact a posterior surface of the at least one lower tooth when accepting the at least one tooth;
- an extension portion that extends away from the tooth engaging portion; and
- a rigid handle that extends down from the extension portion and ends in a caudal end that extends back toward the tooth engaging portion;
- wherein the caudal end of the handle is aligned with the contact surface of the at least one groove of the tooth engaging portion such that force from pulling the caudal end of the handle downward, when the tooth engaging portion is accepting the at least one lower tooth, is directed to the at least one lower tooth in a direction along the longitudinal axis of the at least one lower tooth,
- wherein at least one of the tooth engaging portion, extension portion, or handle comprise at least one suction channel.

34. A device as in claim 33, wherein the handle and the extension portion comprise a solid, one-piece construct.

35. A device as in claim 34, wherein at least part of the tooth engaging portion comprises the solid, one-piece construct.

36. A device as in claim 35, wherein the tooth engaging portion comprises:
- a distal end of the solid, one-piece construct; and
- a piece of material attached to the distal end of the one-piece construct, wherein the piece of material is softer than the one-piece construct.

37. A device as in claim 33, wherein the extension portion is curved.

38. A device as in claim 33, wherein the extension portion and the tooth engaging portion are forked, and wherein a space between two prongs of the tooth engaging portion and the extension portion is configured to accept a suction tube.

39. A device as in claim 33, wherein the caudal end of the handle comprises a finger loop through which a finger of the patient or a medical professional may be extended to facilitate application of downward force.

40. A device as in claim 33, further comprising a tissue displacement member coupled with at least one of the tooth engaging portion or the extension portion, for displacing at least one of a cheek or a tongue of the patient.

* * * * *